(12) United States Patent  
Feyereisen et al.

(10) Patent No.: US 7,132,590 B2
(45) Date of Patent: Nov. 7, 2006

(54) METHODS OF MAKING MALE-STERILE PLANTS BY UNDEREXPRESSING ALLENE OXIDE SYNTHASE

(75) Inventors: Rene Feyereisen, Valbonne (FR); Joon-Hyun Park, Westlake Village, CA (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 491 days.

(21) Appl. No.: 10/322,924

(22) Filed: Dec. 18, 2002

(65) Prior Publication Data

US 2003/0217388 A1  Nov. 20, 2003

Related U.S. Application Data

(60) Provisional application No. 60/344,061, filed on Dec. 26, 2001, provisional application No. 60/342,264, filed on Dec. 18, 2001.

(51) Int. Cl.
*A01H 5/00* (2006.01)
*C12N 15/82* (2006.01)

(52) U.S. Cl. ........................ 800/303; 800/285
(58) Field of Classification Search ............ None
See application file for complete search history.

(56) References Cited

U.S. PATENT DOCUMENTS

| | | | |
|---|---|---|---|
| 4,801,340 A | 1/1989 | Inoue et al. | |
| 5,034,323 A | 7/1991 | Jorgensen et al. | |
| 5,231,020 A | 7/1993 | Jorgensen et al. | |
| 5,283,184 A | 2/1994 | Jorgensen et al. | |
| 6,177,616 B1 | 1/2001 | Bartsch et al. | |
| 6,184,439 B1 | 2/2001 | Fabijanski et al. | |
| 6,198,026 B1 | 3/2001 | Fabijanski et al. | |
| 6,215,045 B1 | 4/2001 | Knox et al. | |

OTHER PUBLICATIONS

Wang et al, 1999, Plant Mol. Biol 40:783-793.*
Laudert et al, 2000, Planta 211:163-165.*
Krysan et al, 1999, Plant Cell 11:2283-2290.*
Arabidopsis Knockout Facility, 1999, http://www.biotech.wisc.edu/NewServicesandResearch/Arabidopsis/IntroductionIndex.html.*
Yang et al, 1990, Devel. Genet. 11:289-293.*
Custers et al, 1999, Protoplasma 208:257-264.*
Adams et al., "Hindered Dialkylamino Nucleoside Phosphite Reagents in the Synthesis of Two DNA 51-Mers," *J. Am. Chem. Soc.*, 1983, 105:661-663.
Ausubel et al., *Current Protocols in Molecular Biology*, John Wiley & Sons, Inc., Media, PA (TOC only).
Avdiushko et al., "Effect of Volatile Methyl Jasmonate on the Oxylipin Pathway in Tobacco, Cucumber, and Arabidopsis," *Plant Physiol.*, 1995, 109(4):1227-1230.

Baldwin et al., "Quantification, correlations and manipulations of wound-induced changes in jasmonic acid and nicotine in *Nicotiana sylvestris*," *Planta*, 1997, 201:397-404.
Bate et al., "Molecular Characterization of an Arabidopsis Gene Encoding Hydroperoxide Lyase, a Cytochrome P-450 That Is Wound Inducible," *Plant Physiol.*, 1998, 117(4):1393-1400.
Bell and Mullet, "Characterization of an *Arabidopsis* Lipoxygenase Gene Responsive to Methyl Jasmonate and Wounding," *Plant Physiol.*, 1993, 103:1133-1137.
Bennett and Wallsgrove, "Tansley Review No. 72 Secondary metabolites in plant defence mechanisms," *New Phytol.*, 1994, 127:617-633.
Bevan et al., "T-DNA of the Agrobacterium TI and RI Plasmids," *Annu. Rev. Genet.*, 1982, 16:357-384.
Bevan, "Binary *Agrobacterium* vectors for plant transformation," *Nucl. Acids. Res.*, 1984, 12:8711-8721.
Biesgen and Weiler, "Structure and regulation of *OPR1* and *OPR2*, two closely related genes encoding 12-oxophytodienoic acid-10,11-reductases from *Arabidopsis thaliana*," *Planta*, 1999, 208:155-165.
Binding, "Regeneration of Plants Horst Binding," *Plant Protoplasts*,1985, CRC Press, Boca Raton, pp. 21-73.
Boulton et al., "Specificity of *Agrobacterium*-mediated delivery of maize streak virus DNA to members of the Gramineae," *Plant Mol. Biol.*, 1989, 12:31-40.
Brisson et al., "Expression of a bacterial gene in plants by using a viral vector," *Nature*, 1984, 310:511-514.
Broglie et al., "Light-Regulated Expression of a Pea Ribulose-1,5-Bisphosphate Carboxylase Small Subunit Gene in Transformed Plant Cells," *Science*, 1984, 224:838-843.
Bustos et al., "Regulation of β-Glucuronidase Expression in Transgenic Tobacco Plants by an A/T-Rich, *cis*-Acting Sequence Found Upstream of a French Bean β-Phaseolin Gene," *Plant Cell*, 1989, 1:839-854.
Carruthers et al., "Chemical Synthesis and Biological Studies on Mutated Gene-control Regions," *Cold Spring Harbor Symp. Quant. Biol.*, 1982, 47:411-418.
Clark-Lewis et al., "Chemical Synthesis, Purification, and Characterization of Two Inflammatory Proteins, Neutrophil Activating Peptide 1 (Interleukin-8) and Neutrophil Activating Peptide 2," *Biochem.*, 1991, 30:3128-3135.
Clough and Bent, "Floral dip: a simplified method for *Agrobacterium*-mediated transformation of *Arabidopsis thaliana*," *Plant J.*, 1998, 16:735-743.

(Continued)

*Primary Examiner*—Anne Kubelik
(74) *Attorney, Agent, or Firm*—Fish & Richardson P.C.

(57) ABSTRACT

Methods are described herein for producing male-sterile plants by underexpressing the allene oxide synthase (CYP74A) gene. Fertility is restored in the plants by treatment with jasmonic acid. Hybrid seed production is simplified and improved by this invention. The present invention also includes plants transformed with an allene oxide synthase coding sequence.

2 Claims, 10 Drawing Sheets

OTHER PUBLICATIONS

Coruzzi et al., "Tissue-specific and light-regulated expression of a pea nuclear gene encoding the small subunit of ribulose-1,5-bisphosphate carboxylase," *EMBO J.*, 1984, 3:1671-1680.

Creelman et al., "Jasmonic acid/methyl jasmonate accumulate in wounded soybean hypocotyls and modulate wound gene expression," *Proc. Natl. Acad. Sci. USA*, 1992, 89:4938-4941.

Creelman and Mullet, "Biosynthesis and Action of Jasmonates in Plants," *Annu. Rev. Plant Physiol.*, 1997, 48:355-381.

Creighton, "Chemical Nature of Polypeptides," *Proteins—Structures and Molecular Principles*, 1983, W.H. Freeman and Co. New York, pp. 34-39.

Creighton, "Proteins," *Proteins—Structures and Molecular Principles*, 1983, W.H. Freeman and Co. New York, pp. 50-60.

Dayhoff, et al., "Matrices for Detecting Distant Relationships," *Atlas of Protein Sequence and Structure*, Suppl. 3, 5:353-358, National Biomedical Research Foundation, Washington, DC.

D'Halluin et al., "Transgenic Maize Plants by Tissue Electroporation," *Plant Cell*, 1992, 4:1495-1505.

Evans et al., "Protoplasts Isolation and Culture," *Handbook of Plant Cell Culture*, 1983, Macmillan Publishing Company, New York, pp. 124-176.

Farmer and Ryan, "Interplant communication: Airborne methyl jasmonate induces synthesis of proteinase inhibitors in plant leaves," *Proc. Natl. Acad. Sci. USA*, 1990, 87:7713-7716.

Farmer et al., "Fatty acid signaling in *Arabidopsis*," *Planta*, 1998, 206:167-174.

Fraley et al., "Expression of bacterial genes in plant cells," *Proc. Natl. Acad. Sci. USA*, 1983, 80:4803.

Fromm et al., "Expression of genes transferred into monocot and dicot plant cells by electroporation," *Proc. Natl. Acad. Sci. USA*, 1985, 82:5824-5828.

Frommer and Starlinger, "DNase I hypersensitive sites in the 5'-region of the maize *Shrunken* gene in nuclei from different organs," *Mol. Gen. Genet.*, 1988, 212(2):351-359.

Gait (ed.), *Oligonucleotide Synthesis a practical approach*, 1984, IRL Press, Oxford, England (TOC only).

Gordon-Kamm et al., "Transformation of Maize Cells and Regeneration of Fertile Transgenic Plants," *Plant Cell*, 1990, 2:603-618.

Gould et al., "Transformation of *Zea mays* L. Using *Agrobacterium tumefaciens* and the Shoot Apex," *Plant Physiol.*, 1991, 95:426-434.

Green et al., "Binding site requirements for pea nuclear protein factor GT-1 correlate with sequences required for light-dependent transcriptional activation of the *rbcS-3A* gene," *EMBO J.*, 1988, 7:4035-4044.

Gribskov, "Sigma factors from *E. coli, B. subtilis*, phage SP01, and phage T4 are homologous proteins," *Nucl. Acids Res.*, 1986, 14(6):6745-6763.

Gundlach et al., "Jasmonic acid is a signal transducer in elicitor-induced plant cell cultures," *Proc. Natl. Acad. Sci. USA*, 1992, 89(6):2389-2393.

Gurley et al., "Upstream Sequences Required for Efficient Expression of a Soybean Heat Shock Gene," *Mol. Cell. Biol.*, 1986, 6:559-565.

Hames and Higgins (eds.), *Nucleic acid hybridisation: a practical approach*, 1985, IRL Press, Oxford, Washington, DC (TOC only).

Harlow and Lane (eds.), *Antibodies: A Laboratory Manual*, 1988, Cold Spring Harbor Laboratory, Cold Spring Harbor, NY (TOC only).

Haseloff et al., "Simple RNA enzymes with new and highly specific endoribonuclease activities," *Nature*, 1988, 334:585-591.

Henry, *Practical Applications of Plant Molecular Biology*, 1997, Chapman & Hall, New York (TOC only).

Hernalsteen et al., "An *Agrobacterium*-transformed cell culture from the monocot *Asparagus officinalis*," *EMBO J.*, 1984, 3:3039-3041.

Hooykass-Van Slogteren et al., "Expression of Ti plasmid genes in monocotyledonous plants infected with *Agrobacterium tumefaciens*," *Nature*, 1984, 311:763-764.

Horsch et al., "A Simple and Generel Method for Transferring Genes into Plants," *Science*, 1985, 227:1229-1231.

Ishiguro et al., "The Defective in Anther Dehiscencei Gene Encodes a Novel Phospholipase A1 Catalyzing the Initial Step of Jasmonic Acid Biosynthesis, Which Synchronizes Pollen Maturation, Anther Dehiscence, and Flower Opening in Arabidopsis," *Plant Cell*, 2001, 13:2191-2209.

Innis et al., (eds.), *PCR Protocols: A Guide to Methods and Applications*, 1990, Academic Press, San Diego, CA (TOC only).

Jones and Sutton, (eds.), *Plant Molecular Biology: Essential Techniques*, 1997, John Wiley & Sons, New York (TOC only).

Jordano et al., "A Sunflower Helianthinin Gene Upstream Sequence Ensemble Contains an Enhancer and Sites of Nuclear Protein Interaction," *Plant Cell*, 1989, 1:855-866.

Kaeppler et al., "Silicon carbide fiber-mediated DNA delivery into plant cells," *Plant Cell Reports*, 1990, 9:415-418.

Klee et al., "*Agrobacterium*-Mediated Plant Transformation and its Further Applications to Plant Biology," *Ann. Rev. Plant Physiol.*, 1987, 38:467-486.

Klein et al., "High-velocity microprojectiles for delivering nucleic acids into living cells," *Nature*, 1987, 327:70-73.

Klein et al., "Transfer of foreign genes into intact maize cells with high-velocity microprojectiles," *Proc. Natl. Acad. Sci. USA*, 1988, 85:4305-4309.

Kramell et al., "Octadecanoid-Derived Alteration of Gene Expression and the "Oxylipin Signature" in Stressed Barley Leaves. Implications for Different Signaling Pathways," *Plant Physiol.*, 2000, 123:177-187.

Kubigsteltig et al., "Structure and regulation of the *Arabidopsis thaliana* allene oxide synthase gene," *Planta*, 1999, 208:463-471.

Laudert et al., "Cloning, molecular and functional characterization of *Arabidopsis thaliana* allene oxide synthase (CYP 74), the first enzyme of the octadecanoid pathway to jasmonates," *Plant Mol. Biol.*, 1996, 31:323-335.

Laudert et al., "Analysis of 12-Oxo-phytodienoic Acid Enantiomers in Biological Samples by Capillary Gas Chromatography-Mass Spectrometry Using Cyclodextrin Stationary Phases," *Anal. Biochem.*, 1997, 246(2):211-217.

Laudert and Weiler, "Allene oxide synthase: a major control point in *Arabidopsis thaliana* octadecanoid signalling," *Plant J.*, 1998, 15:675-684.

Laudert et al., "Transgenic *Nicotiana tabacum* and *Arabidopsis thaliana* plants overexpressing allene oxide synthase," *Planta*, 2000, 211:163-165.

Lee et al., "Jasmonate signalling can be uncoupled from abscisic acid signalling in barley: identification of jasmonate-regulated transcripts which are not induced by abscisic acid," *Planta*, 1996, 199:625-632.

Liu et al., "Efficient isolation and mapping of *Arabidopsis thaliana* T-DNA insert junctions by thermal asymmetric interlaced PCR," *Plant J.*, 1995, 8:457-463.

Matsui et al., "Bell pepper fruit fatty acid hydroperoxide lyase is a cytochrome P450 (CYP74B)," *FEBS Lett.*, 1996, 394(1):21-24.

Matsui et al., "Molecular Cloning and Expression of *Arabidopsis* Fatty Acid Hydroperoxide Lyase," *Plant Cell Physiol.*, 1999, 40(5):477-481.

McConn et al., "Jasmonate is essential for insect defense in *Arabidopsis*," *Proc. Natl. Acad. Sci. USA*, 1997, 94:5473-5477.

Meier et al., "Elicitor-Inducible and Constitutive in Vivo DNA Footprints Indicate Novel *cis*-Acting Elements in the Promoter of a Parsley Gene Encoding Pathogenesis-Related Protein 1," *Plant Cell*, 1991, 3:309-315.

Merrifield, "Solid Phase Peptide Synthesis. I. The Synthesis of a Tetrapeptide," *J. Am. Chem. Soc.*, 1963, 85:2149-2156.

Messing et al., "Plant Gene Structure," *Genetic Engineering of Plants*, 1983, Kosuge et al. (eds.), pp. 211-227.

Meyer, "Transcriptional transgene silencing and chromatin components," *Plant Mol. Biol.*, 2000, 43:221-234.

Napoli et al., "Introduction of a Chimeric Chalcone Synthase Gene into Petunia Results in Reversible Co-Suppression of Homologous Genes *in trans*," *Plant Cell*, 1990, 2:279-289.

Norman et al., "Oligogalacturonide-Mediated Induction of a Gene Involved in Jasmonic Acid Synthesis in Response to the Cell-Wall-Degrading Enzymes of the Plant Pathogen *Erwinia carotovora*," *Mol. Plant Microbe Interact.*, 1999, 12(7):640-644.

Ozawa et al., "Involvement of Jasmonate- and Salicylate-Related Signaling Pathways for the Production of Specific Herbivore-Induced Volatiles in Plants," *Plant Cell Physiol.*, 2000, 41:391-398.

Paquette et al., "Intron-Exon Organization and Phylogeny in a Large Superfamily, the Paralogous Cytochrome P450 Genes of *Arabidopsis thaliana*," *DNA Cell Biol.*, 2000, 19:307-317.

Paszkowski et al., "Direct gene transfer to plants," *EMBO J.*, 1984, 3:2717-2722.

Potrykus et al., "Molecular and general genetics of a hybrid foreign gene introduced into tobacco by direct gene transfer," *Molec. Gen. Genet.*, 1985, 199:169-177.

Perbal, *A Practical Guide to Molecular Cloning*, 1984, John Wiley & Sons, New York (TOC only).

Reymond et al., "Differential Gene Expression in Response to Mechanical Wounding and Insect Feeding in Arabidopsis," *Plant Cell*, 2000, 12:707-719.

Richard et al., "Induction of Chalcone Synthase Expression in White Spruce by Wounding and Jasmonate," *Plant Cell Physiol.*, 2000, 41:982-987.

Rogers et al., "Gene Transfer in Plants: Production of Transformed Plants Using Ti Plasmid Vectors," *Methods Enzymol.*, 1986, 118:627-641.

Sambrook et al., *Molecular Cloning: A Laboratory Manual*, 2nd Edition, 1989, Cold Spring Harbor Laboratory Press, Cold Spring Harbor, NY (TOC only).

Sanders et al., "The Arabidopsis *Delayed Dehiscencei* Gene Encodes an Enzyme in the Jasmonic Acid Synthesis Pathway," *Plant Cell*, 2000, 12:1041-1061.

Schittko et al., "Eating the evidence? *Manduca sexta* larvae can not disrupt specific jasmonate induction in *Nicotiana attenuata* by rapid consumption," *Planta*, 2000, 210:343-346.

Schuler, "Plant Cytochrome P450 Monooxygenases," *Crit. Rev. Plant Sci.*, 1996, 15:235-284.

Sembdner and Parthier, "The Biochemistry and the Physiological and Molecular Actions of Jasmonates," *Annu. Rev. Plant Physiol. Plant Mol. Biol.*, 1993, 44:569-589.

Sheehy et al., "Reduction of polygalacturonase activity in tomato fruit by antisense RNA," *Proc. Natl. Acad. Sci. USA*, 1988, 85:8805-8809.

Shimamoto, "Fertile transgenic rice plants regenerated from transformed protoplasts," *Nature*, 1989, 338:274-276.

Sikorski et al., "*In Vitro* Mutagenesis and Plasmid Shuffling: From Cloned Gene to Mutant Yeast," *Meth. Enzymol.*, 1991, 194:302-318.

Smith and Waterman, "Comparison of Biosequences," *Advances in Applied Mathematics*, 1981, 2:482-489.

Smyth et al., "Early Flower Development in *Arabidopsis*," *Plant Cell*, 1990, 2:755-767.

Stintzi et al., "Plant defense in the absence of jasmonic acid: The role of cyclopentenones," *Proc. Natl. Acad. Sci. USA*, 2001, 98:12837-12842.

Takamatsu et al., "Expression of bacterial chloramphenicol acetyltransferase gene in tobacco plants mediated by TMV-RNA," *EMBO J.*, 1987, 6:307-311.

Thomma et al., "Requirement of Functional *Ethylene-Insensitive 2* Gene for Efficient Resistance of Arabidopsis to Infection by *Botrytis cinerea*," *Plant Physiol.*, 1999, 121:1093-1101.

Utsugi et al., "*Arabidopsis thaliana* vegetative storage protein (VSP) genes: gene organization and tissue-specific expression," *Plant Mol. Biol.*, 1998, 38:565-576.

van Wees et al., "Enhancement of induced disease resistance by simultaneous activation of salicylate- and jasmonate-dependent defense pathways in *Arabidopsis thaliana*," *Proc. Natl. Acad. Sci. USA*, 2000, 97:8711-8716.

Wang et al., "Involvement of Phospholipase D in Wound-Induced Accumulation of Jasmonic Acid in Arabidopsis," *Plant Cell*, 2000, 12:2237-2246.

Wasternack and Parthier, "Jasmonate-signalled plant gene expression," *Trends Plant Sci.*, 1997, 2:302-307.

Weber et al., "Dinor-oxo-phytodienoic acid: A new hexadecanoid signal in the jasmonate family," *Proc. Natl. Acad. Sci. USA*, 1997, 94:10473-10478.

Weichert et al., "Lipids and Signalling: Oxylipins 3-Functional Aspects," *Biochem. Soc. Trans.*, 2000, 28:861-862.

Weising et al., "Foreign Genes in Plants: Transfer, Structure, Expression, and Applications," *Ann. Rev. Genet.*, 1988, 22:421-477.

Weissbach and Weissbach, (eds.), "Gene Transfer in Plants: Production of Transformed Plants Using Ti Plasmid Vectors," *Methods for Plant Molecular Biology*, 1988, Academic Press, New York, Section VIII, pp. 421-463.

Werck-Reichhart and Feyereisen, "Cytochromes P450:a success story," *Genome Biology*, 2000, 1:3003.1-3003.9.

Winkler et al., "Systematic Reverse Genetics of Transfer-DNA-Tagged Lines of Arabidopsis," *Plant Physiol.*, 1998, 118:743-750.

Winz and Baldwin, "Molecular Interactions between the Specialist Herbivore *Manduca sexta* (Lepidoptera, Sphingidae) and Its Natural Host *Nicotiana attenuata*. IV. Insect-Induced Ethylene Reduces Jasmonate-Induced Nicotine Accumulation by Regulating Putrescine *N*-Methyltransferase Transcripts," *Plant Physiol.*, 2001, 125:2189-2202.

Zhang et al., "DNA Sequences That Activate Isocitrate Lyase Gene Expression during Late Embryogenesis and during Postgerminative Growth," *Plant Physiol.*, 1996, 110:1069-1079.

Zhao and Ma, "Male fertility: A case of enzyme identity," *Curr. Biol.* 2000, 10:R904-R907.

"pD991-AP3 Final seq" obtained from the internet on Jan. 24, 2006 at http://biotech.wisc.edu/newservicesandresearch/arabidopsis/pD991-AP3_finalseq.html, 3 pages.

Agrawal et al., "Molecular cloning and mRNA expression analysis of the first rice jasmonate biosynthetic pathway gene allene oxide synthase," *Plant Physiol. Biochem.*, 2002, 40:771-782.

Froehlich et al., "Tomato Allene Oxide Synthase and Fatty Acid Hydroperoxide Lyase, Two Chytochrom P450s Involved in Oxylipin Metabolism, Are Targeted to Different Membranes of Chloroplast Envelope," *Plant Physiology*, Jan. 2001, 125:306-317.

Harms et al., "Expression of a Flax Allene Oxide Synthase cDNA Leads to Increased Endogenous Jasmonic Acid (JA) Levels in Transgenic Potato Plants but Not to a Corresponding Activation of JA-Responding Genes," *The Plant Cell*, Oct. 1995, 7:1645-1654.

Howe et al., "Cytochrome P450-Dependent Metabolism of Oxylipins in Tomato. Cloning and Expression of Allene Oxide Synthase and Fatty Acid Hydroperoxide Lyase," *Plant Physiology*, Jun. 2000, 123:711-724.

Lau et al., "Low Carbon Monoxide Affinity Allene Oxide Synthase is the Predominant Cytochrome P450 in Many Plant Tissues," *Biochemistry*, 1993, 32:1945-1950.

Maucher et al., "Allene oxide synthases of barley (Hordeum vulgare cv. Salome): tissue specific regulation in seedling developments," *The Plant Journal*, 2000, 21(2):199-213.

Pan et al, "The Major Protein of Guayule Rubber Particles Is a Cytochrome P450," *The Journal of Biological Chemistry*, Apr. 14, 1995, 270(15):8487-8494.

Park et al., "A knock-out mutation in allene oxide synthase results in male sterility and defective wound signal transduction in *Arabidopsis* due to block in jasmonic acid biosynthesis," *The Plant Journal*, 2002, 31(1):1-12.

Werck-Reichart et al., "Cytochromes P450," *American Society of Plant Biologists*, 2002, 28 pages.

Schuler et al., "Functional Genomics of P450s," *Annu. Rev. Plant Biol.*, 2003, 54:629-667.

Song et al., "Molecular cloning of an allene oxide synthase: A cytochrome P450 specialized for the metabolism of fatty acid hydroperoxides," *Proc. Natl. Acad. Sci. USA*, Sep. 1993, 90:8519-8523.

Utsunomiya et al., "Purification and inactivation by substrate of an allene oxide synthase (CYP74) from corn (*Zea mays* L.) seeds," *Phytochemistry*, 2000:319-323.

GenBank Accession No. Y12636, dated Nov. 2, 1998.
GenBank Accession No. Z97339, dated Apr. 18, 2005.
GenBank Accession No. AF234296, dated Apr. 24, 2000.

* cited by examiner

Figure 8 (page 1)

```
   1 aagctttacc aaaaaagtac aatggtgata tatatttggt tagtttgacc agtgagaatg
  61 cattttatca catttatgta aaccactcaa caaagaacct ctagcaagcg tcggacaaga
 121 agtttaagat tactaaggcc agaattaatt actaccttgt tcacatgttg tatgatcatc
 181 gtagcataat gtcttagaac aaacagatca gctacatgtt aagctctacg accaaaatgt
 241 tgaagggctc gaggctaatg tagtttggtg tctcttatga aaaagctact ccacagaggc
 301 ttcaaatatt atcttttaag cacaagacac atgcgattaa agtagcattg aggacttcgt
 361 gattgtgatt acttccatgt aacgccctcg atgcaaatta aaaatgttgt tttcatcaat
 421 agccactcct aactcggaag tgtttagtta tgacaatcaa aaacttaaga gaattttctg
 481 tgtattccaa tatgttatga ggtttattca aagagaagga gacctaagta ttttctttcc
 541 aacaaggcaa aaaacaggta aacgcttgag acaaatatta tcatgtttgt ccaaaaatag
 601 tgagtatcat gtgaataatt tagaagctag atatgttcgt caataaacaa taaaatgcgc
 661 taggatacaa aacgaacgct tgggacgtgt tttaggtaca aaacttcaaa aaaatcttta
 721 tcgagacaga tttccagata aaatacacat accattttaa caacgtgtgt gtttatacaa
 781 aaataacaaa atattaattt tacgatttga agatatatat tgtcagaagg ggaaaagaaa
 841 aaaacaaaac aaaaagatac aaaacagagt aacaaactct ataaaatatg ataatataat
 901 acataattgg gaaaatgact aaacattatc tctgcctttt ggaactcatc aataattata
 961 tattttttta tttctcataa aagtcaaaac tatcaattct taaattcatt ctaattcact
1021 caactttttt ttataaaaaa atatctatat taagttctcg atattattta cttccattaa
1081 tttatcaaat gatttTggta tagaatcaac ttataatcat ggatcaagtc gtggaataac
1141 atatgctcaa gggatggagc taaagtgca gtctaccaaa cctcaagtgt tgtaacttt
1201 gtataagcta ggcctccgat tattaactga atcggttttt ctggatcaaa ccaaactgag
1261 atttggggtt tggttaaccg tccggtttat aagagtcagc cagtcagtta gatttgaaa
1321 taaggtcgga taacagtttg gtttggttta tcgaaccaaa cggttaacca tttgtttaaa
1381 attttccaat ttaataattt tacggatatt ttacgtaatg atatcaaaaa ttcttcaaaa
1441 cactacgtga accaaaaaaa aactattcaa atattttaa agtctcaaat gcttgtataa
1501 actattgata gtacattttc aggatatatt ataagaagag gaatattaaa caaagaaaca
1561 aaaatacaaa acagagcaac aagctcgata aaatatgaga ataaatagta ccaactttta
1621 cacaacaaaa acattaccaa ttttttaata tgtcagaaaa aataaaaaaa gtaccaactt
1681 tataaaatga aggaaaaaag agtcaaagca cgtggctaaa tgaatcggcc ggtggccaga
1741 gtctccaata gatctcttta ataactgcgt ggtctgaaaa aggaatcttc cttccacggc
1801 cactaaattc actattttca ttcacattta ttatttttct ttataaatac aaattcattt
1861 ctacacaata atcattcaat acacataatt tacttctttc tttataacta ccatattctc
1921 aatcacaaca ctcgccactg tttcgaatag atggcttcta tttcaacccc ttttccgatt
1981 tctctccacc caaaaaccgt acgatcaaag ccgttgaaat tccgagtttt gacccgtccg
2041 atcaaagctt ccgggtcaga aactcctgat ctaaccgtag cgacacgaac cggatccaaa
2101 gatctcccga tccgaaacat accgggaaac tacggtttac caatcgtagg accaatcaaa
2161 gaccgttggg attacttta cgaccaagga gctgaagagt tcttcaaatc acgaatccgt
2221 aaatacaact ccacggtgta cagagtcaac atgccaccgg gagcttttat cgccgagaat
2281 ccacaagtcg tggctttact cgacggtaaa agcttccgg ttttattcga tgtcgataaa
2341 gtcgaaaaga aagatctttt caccggtact tacatgccgt caacggaact aaccggaggc
2401 taccgtatcc tctcgtacct cgatccatcg gagcctaaac acgaaaagct caaaaatctc
2461 cttttcttcc tcctcaagtc atctcgaaac cggatcttcc ctgagtttca agctacttac
2521 tccgagcttt tcgattcttt ggagaaagag ctttcccta aagggaaagc ggatttcggc
2581 ggttccagcg acggaaccgc ctttaatttc ttggctcgag ctttctacgg gacgaatccc
2641 gcagatacaa agctcaaagc cgacgctccg ggtttgatca ctaaatgggt tttattcaat
2701 ctccatccat tactctctat tggtttaccg agagttatag aagaacctct catccataca
2761 tttagtctac caccggcgtt agtcaaatct gattaccaga gactctacga gtttttctta
2821 gaatccgccg gtgagattct cgttgaagcc gataaattgg gtatctcacg agaagaagct
2881 actcacaatc ttctcttcgc cacgtgcttc aacacgtggg gtgggatgaa gatttttgttt
2941 ccgaatatgg ttaaacgtat cgggcgggcg ggtcatcaag ttcataaccg attagcggag
3001 gagattagat ctgtgattaa atccaacggc ggagaactca cgatgggagc gattgagaaa
3061 atggagttaa ccaaatcagt ggtttacgaa tgtctccggt ttgaaccacc ggttacggct
3121 caatacggta gagcgaagaa ggatctggtt atcgaaagcc acgacgcggc gtttaaagtc
3181 aaagccggtg aaatgcttta cggttatcaa ccgttggcga cgagagatcc gaagattttt
```

Figure 8 (page 2)

```
3241 gatcgggcgg atgagtttgt gccggagaga ttcgtcggag aagaaggaga gaagcttttg
3301 aggcatgtgt tgtggtcgaa tggaccggag acggagactc cgacggtggg gaataaacaa
3361 tgcgccggta aggattttgt tgttttggtg gcgaggttgt ttgtgattga gattttccgg
3421 cgatatgatt cgtttgatat tgaggttggt acgtcgccgt taggaagctc cgttaatttc
3481 tcgtcgttaa ggaaagctag cttttaggag ccaagggtaa atttgtaatt gtatatgttc
3541 gcacctgtgt agtccatctg ttttcttgtt ccagtttcgt gaatttgag aaaatgttgt
3601 ataatctgtt gctgctctac atgttcgttt ttttgtcata atattaaagt tcaagctggt
3661 aataagtatt tacaaatctg tgagataatt tcaaatacac aagagcatat tctttataaa
3721 aaaagcacga gttttttaca ctcaaatatt ttttgagcct gtgaataata gggttttttt
3781 aaccattgtt tttattttgt tagtgacgaa acaaaataac aaaaatatca ccgttaaagt
3841 ttgattatga gatgttataa aagagtgtat tttcctgcat accaaaataa ttcttgtact
3901 tttataaaac cgaatgtttc cgtttatata gtgcaataat ttttagaat atttgtttta
3961 ataatoccca tacacaattt tctgttttaa gccttttatg tattatcgtc agctttctta
4021 atgaagataa taaaagaaat cttctgaaag atggttagat ggggctggta atttggagtt
4081 ttgcttatct ctctctggtt aagtctcttt ccttgcgttg tgtggagcct atgtctatct
4141 ctcggtgacg actgatgagt gtctagaagt gatagagtct agggatcc
```

Figure 9

```
  1 masistpfpi slhpktvrsk plkfrvltrp ikasgsetpd ltvatrtgsk dlpirnipgn
 61 yglpivgpik drwdyfydqg aeeffksrir kynstvyrvn mppgafiaen pqvvalldgk
121 sfpvlfdvdk vekkdlftgt ympsteltgg yrilsyldps epkheklknl lffllkssrn
181 rifpefqaty selfdsleke lslkgkadfg gssdgtafnf larafygtnp adtklkadap
241 glitkwvlfn lhpllsiglp rvieepliht fslppalvks dyqrlyeffl esageilvea
301 dklgisreea thnllfatcf ntwggmkilf pnmvkrigra ghqvhnrlae eirsviksng
361 geltmgaiek meltksvvye clrfeppvta qygrakkdlv ieshdaafkv kagemlygyq
421 platrdpkif dradefvper fvgeegekll rhvlwsngpe tetptvgnkq cagkdfvvlv
481 arlfvieifr rydsfdievg tsplgssvnf sslrkasf
```

METHODS OF MAKING MALE-STERILE PLANTS BY UNDEREXPRESSING ALLENE OXIDE SYNTHASE

CROSS-REFERENCE TO RELATED APPLICATIONS

The present application claims the benefit of U.S. Ser. No. 60/342,264 filed Dec. 18, 2001 and U.S. Ser. No. 60/344,061 filed Dec. 26, 2001, which applications are hereby incorporated by reference in their entireties for all purposes.

TECHNICAL FIELD

The present invention relates to novel methods of regulating plant phenotypes, in particular male sterility. The invention relates to methods of controlling reproduction in plants by, for example, affecting expression of allene oxide synthase (AOS) and/or hydroperoxide lyase (HPL). The invention further relates to affecting other plant phenotypes, such as expression of defense-related genes and pathogen resistance.

BACKGROUND

Production of hybrid seed for commercial sale is a large industry. Hybrid plants, grown from hybrid seed, benefit from the heterotic effects of crossing two genetically distinct breeding lines (i.e., hybrid vigor). Typically, the agricultural performance of such hybrid offspring is superior to both parents, for example, in vigor, and yield. This improved performance of hybrid seed varieties, relative to open-pollinated varieties, makes hybrid seed more attractive for farmers to cultivate. To produce hybrid seed that is not contaminated with selfed seed pollination, methods must be employed to ensure cross-pollination and not self-pollination. Historically, pollination control mechanisms have been mechanical, chemical, and/or genetic.

Simple mechanical methods for hybrid seed production typically can only be used if the selected plant species has spatially separate male and female flowers or if the species has separate male and female plants. For example, corn plants have pollen producing male flowers in an inflorescence at the apex of the plant and female flowers in the axils of leaves along the stem. Out-crossing can be insured by mechanical de-tasselling of female plants. Such de-tasselling prevents selfing. However, most major crop plants have both functional male and female organs within the same flower. Accordingly, emasculation of these crop plants is not a simple procedure. It is possible to hand remove the pollen forming organs before pollen is shed, however, this is a labor intensive and expensive form of hybrid seed production.

A second method for the production of hybrid seed is to use chemicals that block or kill viable pollen formation. Such chemicals (gametocides) are used to provide temporary male-sterility. Commercial production of hybrid seed using gametocides is limited by (i) the expense and availability of the chemicals, and (ii) the reliability and length of action of the applications. When plants have extended flowering periods, gametocides are typically not effective because new flowers are produced that are not affected by previous treatment. Repeated application of chemicals is impractical primarily because cost becomes prohibitive.

Other methods of commercial hybrid seed production for field crops rely on a genetic methods of pollination control. In such methods, plants that are used as females (i) fail to make pollen, (ii) fail to shed pollen, or (iii) produce pollen biochemically unable to provide self-fertilization. Plants unable to biochemically self-pollinate are termed self-incompatible plants. Numerous difficulties are associated with the use of self-incompatibilities, including, propagation and availability of the self-incompatible female line, and stability of the self-incompatibility. Self-incompatible systems that can be deactivated are often vulnerable to stressful climatic conditions, where such environmental stresses reduce the effectiveness of the biochemical self-pollination block.

Further methods of commercial hybrid seed production include systems of pollen control based on genetic mechanisms that cause male sterility. Such systems are generally of two types: (i) nuclear or genic male sterility—the failure of pollen formation because of, typically, mutations in one or more nuclear genes; or (ii) cytoplasmic male sterility (CMS)—pollen formation is blocked or aborted as the result of a defect in a cytoplasmic organelle, typically, the mitochondria.

Nuclear sterility can be either dominant or recessive. Dominant sterility can only be used for hybrid seed formation when propagation of the female line is possible, for example, using in vitro clonal propagation. Recessive sterility can be used when sterile and fertile plants are easily discriminated, for example, based on plant phenotypes. Commercial utility of nuclear sterility systems is limited by the expense of clonal propagation and roguing the female rows of self-fertile plants.

Many successful hybridization schemes involve the use of cytoplasmic male sterility. For example, a specific mutation in the mitochondria can, when in a selected nuclear background, lead to the failure of mature pollen formation. Alternately, the nuclear background can compensate for the cytoplasmic mutation resulting in normal pollen formation. A nuclear trait that allows pollen formation in plants having CMS mitochondria, that is, restoration of fertility, is typically called a "restorer gene." Generally the use of CMS for commercial seed production involves the use of three breeding lines, (i) a male-sterile line (female parent), (ii) a maintainer-line isogenic to the male-sterile line but which contains fully functional mitochondria, and (iii) the male parent line. The male parent line may carry a specific restorer gene(s). In this case the male parent line is usually designated a "restorer line" that imparts fertility to the hybrid seed.

For crops for which seed recovery from the hybrid is unimportant, for example, vegetables, a CMS system can be used without restoration. However, for crops wherein the fruit or seed of the hybrid is the commercial product, then the fertility of the hybrid seed must be restored by specific restorer genes in the male parent or the male-sterile hybrid must be pollinated. Pollination of non-restored hybrids is typically achieved by including, with the hybrid plants, a small percentage of male fertile plants. These male fertile plants effect pollination. In most species, the CMS trait is inherited maternally. This is one restriction of such systems.

A desirable system for hybrid seed production in any crop would be a form of genic male sterility that could be regulated to allow controlled male fertility for the propagation of the female line. The invention described herein provides such a system.

SUMMARY OF THE INVENTION

The present invention is premised, in part, on the isolation of an *Arabidopsis* knock-out mutant defective in the JA biosynthetic gene, CYP74A, allene oxide synthase (AOS)

and the discovery that this male sterile mutant can be completely rescued by the exogenous application of jasmonates or by complementation by constitutive expression of the AOS gene. Jasmonates (JAs) play essential roles in pollen maturation and dehiscence and wound-induced defense against biotic attackers. Using reverse genetics screening methods, the inventors isolated an *Arabidopsis* in which the CYP74 enzyme (which catalyzes the first committed step in the JA-specific biosynthetic pathway, dehydration of 13-(S)-hydroperoxylinolenic acid to 12,13-epoxy-linolenic acid (allene oxide)) is defective. Endogenous JA levels, which increase 100-fold 1 h after wounding in wild-type plants, do not increase after wounding of the aos mutant. In addition, the mutant showed severe male sterility due to defects in anther and pollen development. the Thus, AOS is critical for the biosynthesis of all biologically active jasmonates. Further, although AOS expression appears to be rate-limiting for JA levels in wounded plants, the AOS hydroperoxide substrate levels appear to be controlled by upstream enzymes (lipoxygenase, phospholipase) determine JA levels in unwounded plants.

In one aspect, the invention includes a transgenic plant with altered CYP74A expression relative to the corresponding wild-type plant. In certain embodiments, CYP74A is over-expressed. In other embodiments, CYP74A is under-expressed.

In another aspect, the invention includes a method of producing a transgenic plant with altered CYP74A expression relative to the wild-type plant, said method comprising: (a) introducing an expression construct that comprises a polynucleotide encoding a CYP74A polypeptide operably linked to a promoter which is capable of over-expressing or under-expressing the polynucleotide into a plant cell to produce a transformed plant cell; and (b) producing a transgenic plant from the transformed plant cell with altered CYP74A expression. For example, CYP74A can be over-expressed or underexpressed. The polynucleotide can be operably linked to a tissue-specific promoter, an inducible promoter or a constitutive promoter.

In another aspect, the invention includes a method of producing a transgenic plant with altered CYP74A expression relative to the wild-type plant, said method comprising: (a) introducing a polynucleotide that inhibits expression of a CYP74A polynucleotide into a plant cell to produce a transformed plant cell; and (b) producing a transgenic plant from the transformed plant cell with altered CYP74A expression. In certain embodiments, the polynucleotide produces a CYP74A antisense molecule. In other embodiments, the polynucleotide produces a gene replacement of wild-type CYP74A with a mutant allele of CYP74A, for example, a deletion mutation.

In another aspect, the invention includes a method of producing hybrid seed from plants of a species of pollen-producing plants that is capable of being genetically transformed. To produce hybrid seeds from self-pollinated plants, it is typically desirable to remove and/or inactivate all male characteristics of the parent. Thus, in certain embodiments, hybrid seeds are produced by removing CYP74A function from the parent plant, for example via insertional mutagenesis, deletion, antisense technology or any other method described herein or in the art. These methods are applicable to any self-compatible plant whose male fertility depends on the availability of jasmonates. Parental lines (e.g., male sterile plants) are preferably maintained by blocking functional CYP74A production.

In another aspect, the invention includes a transformed plant containing a recombinant DNA molecule which comprises (1) an antisense DNA sequence the transcript of which is complimentary to mRNA encoded by CYP74A, and (2) a promoter that functions in said plant cell to cause transcription of said antisense DNA sequence into RNA. In certain embodiments, the promoter preferentially transcribes said antisense DNA in cells critical to pollen development or function.

In yet another aspect, described herein are hybrid seeds containing a recombinant DNA molecule which comprises (1) an antisense DNA sequence the transcript of which is complimentary to mRNA encoded by a CYP74A gene, and (2) a promoter that functions in said plant cell to cause transcription of said antisense DNA sequence into RNA is provided. In certain embodiments, the promoter preferentially transcribes said antisense DNA in cells critical to pollen development or function.

These and other objects, aspects, embodiments and advantages of the present invention will readily occur to those of ordinary skill in the art in view of the disclosure herein.

BRIEF DESCRIPTION OF THE DRAWINGS

FIG. 8 depicts the nucleotide sequence (SEQ ID NO:1) of native CYP74A gene locus, AOS gene, derived from *Arabidopsis thalianna* (GenBank Accession No. Y12636). In the figure, a transcription initiation signal is located from approximately bases 1,842 to 1,849, the wild-type mRNA corresponds to sequences from nucleotide position approximately 1,874 to 3,741, and the AOS protein coding sequences are from nucleotide position 1,951 to 3,507.

FIG. 9 depicts the amino acid sequence (SEQ ID NO:2) of the protein product of the native CYP74A, AOS gene derived from *Arabidopsis thalianna* (GenBank Accession No. CAA73184).

DETAILED DESCRIPTION

Figure 1:
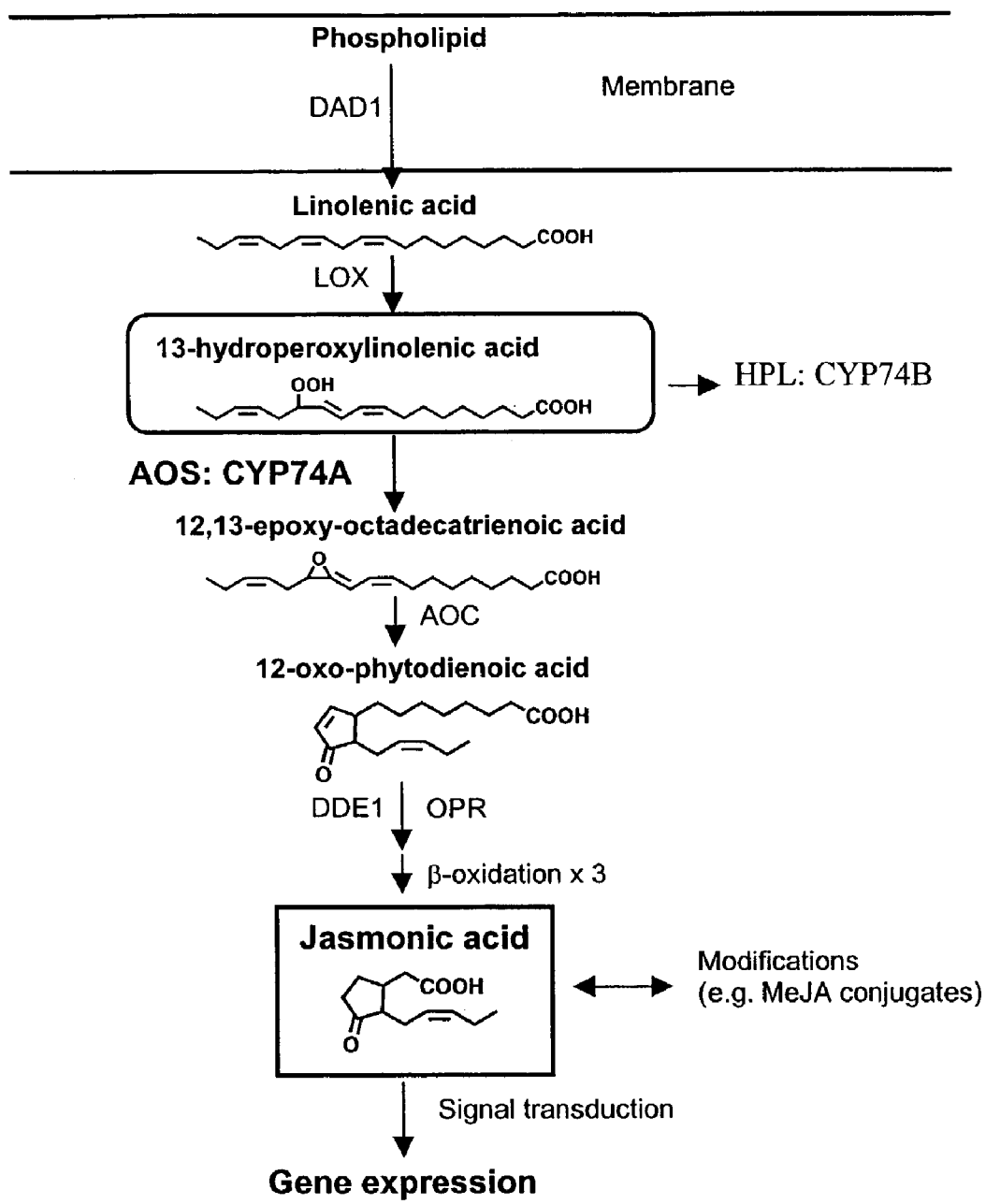
FIG. 1 presents a diagram of jasmonic acid biosynthetic pathway. Linolenic acid (18:3) is released from membrane phospholipid by a lipolytic enzyme (DAD1) and is converted to the allene oxide (12,13-epoxy-octadecatrienoid acid) by a lipoxygenase (LOX) and allene oxide synthase (AOS), a member of the cytochrome P450 family (CYP74A). One cyclization, one reduction, and three rounds of β-oxidation steps are needed to generate jasmonic acid, the end product of the pathway. In the figure, the abbreviations used are defined as follows: DAD1: defective in anther dehiscence1; LOX: lipoxygenase; AOS: allene oxide synthase; AOC: allene oxide cyclease; OPR: 12-oxo-phytodienoic acid-10,11-reductase; DDE1: delayed dehiscence1.

Before describing the present invention in detail, it is to be understood that this invention is not limited to particularly exemplified molecules or process parameters as such may, of course, vary. It is also to be understood that the terminology used herein is for the purpose of describing particular embodiments of the invention only, and is not intended to be limiting. In addition, the practice of the present invention will employ, unless otherwise indicated, conventional methods of plant biology, virology, microbiology, molecular biology, recombinant DNA techniques and immunology all of which are within the ordinary skill of the art. Such techniques are explained fully in the literature. See, e.g., Evans, et al., *Handbook of Plant Cell Culture* (1983, Macmillan Publishing Co.); Binding, *Regeneration of Plants, Plant Protoplasts* (1985, CRC Press); Sambrook, et al., *Molecular Cloning: A Laboratory Manual* (2nd Edition, 1989); *DNA Cloning: A Practical Approach*, vol. I & II (D. Glover, ed.); *Oligonucleotide Synthesis* (N. Gait, ed., 1984); *A Practical Guide to Molecular Cloning* (1984); and *Fundamental Virology*, 2nd Edition, vol. I & II (B. N. Fields and D. M. Knipe, eds.); Ausubel, F. M., et al., *CURRENT PROTOCOLS IN MOLECULAR BIOLOGY*, John Wiley and Sons, Inc., Media Pa.; *Plant Molecular Biology: Essential Techniques*, P. G. Jones and J. M. Sutton, New York, J. Wiley, 1997; Miglani, Gurbachan *Dictionary of Plant Genetics and Molecular Biology*, New York, Food Products Press, 1998; Henry, R. J., *Practical Applications of Plant Molecular Biology*, New York, Chapman & Hall, 1997.

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

1. Definitions

In describing the present invention, the following terms will be employed, and are intended to be defined as indicated below.

The terms "nucleic acid molecule" and "polynucleotide" are used interchangeably and refer to a polymeric form of nucleotides of any length, either deoxyribonucleotides or ribonucleotides, or analogs thereof. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including e.g., nucleases, toxins, antibodies, signal peptides, poly-L-lysine, etc.), those with intercalators (e.g., acridine, psoralen, etc.), those containing chelates (e.g., metals, radioactive metals, boron, oxidative metals, etc.), those containing alkylators, those with modified linkages (e.g., alpha anomeric nucleic acids, etc.), as well as unmodified forms of the polynucleotide. Polynucleotides may have any three-dimensional structure, and may perform any function, known or unknown. Nonlimiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

Techniques for determining nucleic acid and amino acid "sequence identity" are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482–489 (1981). This algorithm can be applied to amino acid sequences by using the scoring matrix developed by Dayhoff, *Atlas of Protein Sequences and Structure*, M. O. Dayhoff ed., 5 suppl. 3:353–358, National Biomedical Research Foundation, Washington, D.C., USA, and normalized by Gribskov, *Nucl. Acids Res.* 14(6):6745–6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.nih.gov/cgi-bin/BLAST.

Alternatively, the degree of sequence similarity between polynucleotides can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 43%–60%, preferably 60–70%, more preferably 70%–85%, more preferably at least about 85%–90%, more preferably at least about 90%–95%, and most preferably at least about 95%–98% sequence identity over a defined length of the molecules, or any percentage between the above-specified ranges, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning, supra; Nucleic Acid Hybridization*, supra.

The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10–14 nucleotides in length having at least approximately 70% sequence identity with the sequence of the selected nucleic acid probe. Stringent hybridization conditions typically allow detection of target nucleic acid sequences of at least about 10–14 nucleotides in length having a sequence identity of greater than about 90–95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, DC; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

A "gene" as used in the context of the present invention is a sequence of nucleotides in a genetic nucleic acid (chromosome, plasmid, etc.) with which a genetic function is associated. A gene is a hereditary unit, for example of an organism, comprising a polynucleotide sequence that occupies a specific physical location (a "gene locus" or "genetic locus") within the genome of an organism. A gene can encode an expressed product, such as a polypeptide or a polynucleotide (e.g., tRNA). Alternatively, a gene may define a genomic location for a particular event/function, such as the binding of proteins and/or nucleic acids, wherein the gene does not encode an expressed product. Typically, a gene includes coding sequences, such as, polypeptide encoding sequences, and non-coding sequences, such as, promoter sequences, polyadenlyation sequences, transcriptional regulatory sequences (e.g., enhancer sequences). Many eucaryotic genes have "exons" (coding sequences) interrupted by "introns" (non-coding sequences). In certain cases, a gene may share sequences with another gene(s) (e.g., overlapping genes).

A "coding sequence" or a sequence which "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence. "Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), translation enhancing sequences, and translation termination sequences. Transcription promoters can include inducible promoters (where expression of a polynucleotide sequence operably linked to the promoter is induced by an analyte, cofactor, regulatory protein, etc.), tissue-specific promoters (where expression of a polynucleotide sequence operably linked to the promoter is induced only in selected tissue), repressible promoters (where expression of a polynucleotide sequence operably linked to the promoter is induced by an analyte, cofactor, regulatory protein, etc.), and constitutive promoters.

A control element, such as a promoter, "directs the transcription" of a coding sequence in a cell when RNA polymerase will bind the promoter and transcribe the coding sequence into mRNA, which is then translated into the polypeptide encoded by the coding sequence.

"Expression enhancing sequences" typically refer to control elements that improve transcription or translation of a polynucleotide relative to the expression level in the absence of such control elements (for example, promoters, promoter enhancers, enhancer elements, and translational enhancers (e.g., Shine and Delagarno sequences).

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

A "heterologous sequence" as used herein typically refers to a nucleic acid sequence that is not normally found in the cell or organism of interest. For example, a DNA sequence encoding a polypeptide can be obtained from a plant cell and introduced into a bacterial cell. In this case the plant DNA sequence is "heterologous" to the native DNA of the bacterial cell.

The "native sequence" or "wild-type sequence" of a gene is the polynucleotide sequence that comprises the genetic locus corresponding to the gene, e.g., all regulatory and open-reading frame coding sequences required for expression of a completely functional gene product as they are present in the wild-type genome of an organism. The native sequence of a gene can include, for example, transcriptional promoter sequences, translation enhancing sequences, introns, exons, and poly-A processing signal sites. It is noted that in the general population, wild-type genes may include multiple prevalent versions that contain alterations in sequence relative to each other and yet do not cause a discernible pathological effect. These variations are designated "polymorphisms" or "allelic variations."

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide.

By "vector" is meant any genetic element, such as a plasmid, phage, transposon, mobile genetic element, cosmid, chromosome, virus etc., which is capable of transferring gene sequences to target cells. Generally, a vector is capable of replication when associated with the proper control elements. Thus, the term includes cloning and expression vehicles, as well as viral vectors and integrating vectors.

As used herein, the term "expression cassette" refers to a molecule comprising at least one coding sequence operably linked to a control sequence which includes all nucleotide sequences required for the transcription of cloned copies of the coding sequence and the translation of the mRNAs in an appropriate host cell. Such expression cassettes can be used to express eukaryotic genes in a variety of hosts such as bacteria, blue-green algae, plant cells, yeast cells, insect cells and animal cells, either in vivo or in vitro. Under the invention, expression cassettes can include, but are not limited to, cloning vectors, specifically designed plasmids, viruses or virus particles. The cassettes may further include an origin of replication for autonomous replication in host cells, selectable markers, various restriction sites, a potential for high copy number and strong promoters.

A cell has been "transformed" by an exogenous polynucleotide when the polynucleotide has been introduced inside the cell. The exogenous polynucleotide may or may not be integrated (covalently linked) into chromosomal DNA making up the genome of the cell. In prokaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

"Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

The term "CYP74A polynucleotide" refers to a polynucleotide derived from the gene encoding the CYP74A polypeptide that encodes a polynucleotide that retains CYP74A enzymatic activity. CYP74A encodes allene oxide synthase. Several CYP74A genes have been isolated including, CYP74A1, characterized in flax, CYP74A2, characterized in rubber plants, and another CYP74A1 characterized in *Arabidopsis*. The term as used herein encompasses a polynucleotide including a native allene oxide synthase sequence, as well as modifications and fragments thereof. The term CYP74A polynucleotide as used herein encompass a polynucleotide including, respectively, a native allene oxide synthase sequence as well as modifications and fragments thereof.

Thus, the terms CYP74A polynucleotide encompasses alterations to the polynucleotide sequences, so long as the alteration results in a molecule displaying CYP74A activity. The activity displayed by mutant molecules is typically not at the same level as the native molecule. Modifications of the polynucleotide sequences described herein typically include deletions, additions and substitutions, to the native CYP74A sequences. These modifications may be deliberate, as through site-directed mutagenesis, or may be accidental, such as through mutations of plants which express the polynucleotide or errors due to PCR amplification. The term encompasses expressed allelic variants of the wild-type sequence which may occur by normal genetic variation or are produced by genetic engineering methods and which result in CYP74A activity.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein. Full-length proteins, analogs, mutants and fragments thereof are encompassed by the definition. The terms also include post-expression modifications of the polypeptide, for example, glycosylation, acetylation, phosphorylation and the like. Furthermore, as ionizable amino and carboxyl groups are present in the molecule, a particular polypeptide may be obtained as an acidic or basic salt, or in neutral form. A polypeptide may be obtained directly from the source organism, or may be recombinantly or synthetically produced (see further below).

The terms "CYP74A analog" refer to derivatives of CYP74A, or fragments of such derivatives, that retain desired function. In general, the term "analog" refers to compounds having a native polypeptide sequence and structure with one or more amino acid additions, substitutions (generally conservative in nature) and/or deletions, relative to the native molecule, so long as the modifications do not destroy desired activity. Preferably, the analog has at least the same activity as the native molecule. Methods for making polypeptide analogs are known in the art in view of the teachings provided herein.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. It is to be understood that the terms include the various sequence polymorphisms that exist, wherein amino acid substitutions in the protein sequence do not affect the essential functions of the protein.

By "purified" and "isolated" is meant, when referring to a polypeptide or polynucleotide, that the molecule is separate and discrete from the whole organism with which the molecule is found in nature; or devoid, in whole or part, of sequences normally associated with it in nature; or a sequence, as it exists in nature, but having heterologous sequences (as defined below) in association therewith. It is to be understood that the term "isolated" with reference to a polynucleotide intends that the polynucleotide is separate and discrete from the chromosome from which the polynucleotide may derive. The term "purified" as used herein preferably means at least 75% by weight, more preferably at least 85% by weight, more preferably still at least 95% by weight, and most preferably at least 98% by weight, of biological macromolecules of the same type are present. An "isolated polynucleotide which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

By "fragment" is intended a polypeptide or polynucleotide consisting of only a part of the intact sequence and structure of the reference polypeptide or polynucleotide, respectively. The fragment can include a 3' or C-terminal deletion or a 5' or N-terminal deletion, or even an internal deletion, of the native molecule. A polynucleotide fragment of a CYP74A sequence will generally include at least about 15 contiguous bases of the molecule in question, more preferably 18–25 contiguous bases, even more preferably 30–50 or more contiguous bases of the CYP74A molecule, or any integer between 15 bases and the full-length sequence of the molecule. Fragments are useful, for example, as oligonucleotide probes to find additional CYP74A sequences, e.g., in different plant species.

Similarly, a polypeptide fragment of a CYP74A molecule will generally include at least about 5–10 contiguous amino acid residues of the full-length molecule, preferably at least about 15–25 contiguous amino acid residues of the full-length molecule, and most preferably at least about 20–50 or more contiguous amino acid residues of the full-length CYP74A molecule, or any integer between 10 amino acids and the full-length sequence of the molecule. Such fragments are useful for the production of antibodies and the like.

By "transgenic plant" is meant a plant into which one or more exogenous polynucleotides have been introduced. Examples of means by which this can be accomplished are described below, and include *Agrobacterium*-mediated transformation, biolistic methods, electroporation, and the like. In the context of the present invention, the transgenic plant contains a CYP74A polynucleotide which is either over- or underexpressed and which confers at least one phenotypic trait to the plant, as described herein. The transgenic plant therefore exhibits altered structure, morphology or biochemistry as compared with a progenitor plant which does not contain the transgene, when the transgenic plant and the progenitor plant are cultivated under similar or equivalent growth conditions. Such a plant containing the exogenous polynucleotide is referred to here as an $R_1$ generation transgenic plant. Transgenic plants may also arise from sexual cross or by selfing of transgenic plants into which exogenous polynucleotides have been introduced. Such a plant containing the exogenous nucleic acid is also referred to here as an $R_1$ generation transgenic plant. Transgenic plants which arise from a sexual cross with another parent line or by selfing are "descendants or the progeny" of a $R_1$ plant and are generally called $F_n$ plants or $S_n$ plants, respectively, n meaning the number of generations.

2. General Overview

CYP74 gene products are involved in the oxylipin pathway in *Arabidopsis* (FIG. 1). The CYP74A gene encodes an allene oxide synthase (AOS) that catalyzes the rate limiting step in the jasmonic acid biosynthesis pathway. AOS is a non-classical cytochrome P450 enzyme in that it catalyzes in the absence of an NADPH-dependent P450 reductase and oxygen (See, Schuler et al. (1996) *Crit. Rev. Plan Sci.* 15:235–284). The metabolic roles of P450s in higher plants include, but are not limited to, involvement in biosynthetic pathways (for example, phenylpropanoids, alkaloids, terpenoids, lipids, phytoalexins, sterols, and phytohormones (e.g., auxin, gibberellic acid, and jasmonic acid)), and catabolic pathways (e.g., oxidative detoxifications of a number of herbicides).

Jasmonates are cyclopentanone derivatives that originate biosynthetically from linolenic acid via an inducible octadecanoid pathway consisting of several enzymatic steps (FIG. 1). Jasmonic acid (JA), the end product of this pathway, its methyl ester (MeJA), and certain (L)-amino acid conjugates, glucose esters and hydroxylated forms are all found in plants (Sembdner and Parthier (1993) *Annu Rev. Plant Physiol.* 54:328–332; Farmer and Ryan (1990) *PNAS USA* 87:7713–7716). Generally, among these jasmonate derivatives, JA and MeJA are referred to as "jasmonates (JAs)" and recognized as the most potent plant growth regulators with signaling properties in various developmentally and environmentally induced changes in gene expression (Baldwin et al. (1997) *Planta* 201:397–404; Creelman and Mullet (1997) *Annu Rev. Plant Physiol.* 48:355–381; Wasternack and Parthier (1997) *Trends Plant Sci* 2:302–307). A recent report shows that cyclopentenone precursors of JA can also regulate wound induction of genes (Stintzi et al. (2001) *PNAS USA* 98:12837–12842).

The role of jasmonates in response to biotic stress, such as insect and fungal attack (Bennett and Wallsgrove (1994) *New Phytol.* 127:617–633; McConn et al. (1997) *PNAS USA* 94:5473–5477; Ozawa et al. (2000) *Plant Cell Physiol.* 41:391–398), and abiotic stress, such as mechanical wounding, have been well documented (Baldwin et al., 1997; Creelman and Mullet; 1997; Reymond et al. (2000) *Plant Cell* 12:707–720; Richard et al., (2000) *Plant Cell Physiol.* 41:982–987) and have implications for biology and agriculture. Also, these JA mediated pathogen- and wound-signal transduction pathways are co-regulated by interactions with other phytohormones (Lee et al. (1996) *Planta* 199:625–632; Thomma et al. (1999) *Plant Physiol* 121:

1093–1102; van Wees et al. (2000) *PNAS USA* 97:8711–8716; Winz and Baldwin (2001) *Plant Physiol* 125:2189–2202.

Linolenic acid, a trienoic fatty acid, serves as the substrate for the biosynthesis of JA (McConn and Browse, 1996). The early steps convert LA to 12-oxo-phytodienoic acid (OPDA) by three enzymes located in the chloroplast, lipoxygenase (LOX), allene oxide synthase (AOS) and allene oxide cyclase (AOC; FIG. 1). OPDA is reduced by a a putative peroxiosome associated enzyme, 12-oxo-phytodienoic acid reductase (OPR) whose product undergoes three cycles of β-oxidation, presumably in the peroxisome, to generate JA (Stinzi and Browse (2000) *PNAS USA* 98:12837–12842).

McConn and Browse (1996) first showed that LA was required for male fertility in *Arabidopsis* by demonstrating that the male sterility in a triple mutant (fad3-2/fad7-2/fad8) lacking hexadecatrienoic acid (16:3) and the LA (18:3) could be rescued by exogenous application of JA. In recent years, mutants with lesions in various JA biosynthetic enzymes have been shown to be defective in pollen maturation and release (Farmer et al. (1998) *Planta* 206:167–174; Sanders et al. (2000) *Plant Cell* 12:1041–1061; Stintzi and Browse (2000) *PNAS USA* 97:12837–12842; Zhao and Ma (2000) *Curr Biol* 10:R904–907; Ishiguro et al. (2001) *Plant Cell* 13:2192–2209). Ishiguro et al. (2001) identified a T-DNA tagged male-sterile mutant (dad1) in which the sterility phenotype could be rescued with exogenous application of LA and JA. The cloned gene shared homology with lipases and was shown to hydrolyze phospholipids. Overexpression of DAD1 resulted in plants that tended to be yellow-green presumably because of excess hydrolysis of phopholipids in the chloroplast membranes, damaging the chloroplasts. Without being bound by one theory, it is postulated that DAD1 is the first committed step to JA synthesis as it catalyzes the release of free LA from cellular lipids (FIG. 1). A knock-out mutant of an enzyme further down in the JA pathway, 12-oxophytodienoic acid-10,11-reductase3 (encoded by the OPR3 gene Sanders et al. 2000; Stinzi and Browse, 2000) also showed severe male sterility due to a defect in the timing of stomium degeneration and the release of pollen. (FIG. 1). The stomium cells eventually degenerate and pollen are released in dde1 plant, but at a later stage of flower development (Sanders et al. 2000). This recovery might be due to the other two OPR isozymes (e.g., OPR1 and OPR2) which, were expressed predominantly in *Arabidopsis* root and only low levels in flowers (Biesgen and Weiler (1999) *Planta* 208:155–165, and/or by the alternative pathway which may generate JAs from 16:3 trienoic acids (Weber et al. (1997) *PNAS USA* 94:10473–10478; Farmer et al., 1998).

To better understand the role of jasmonate signaling in pollen and anther development, we screened for allene oxide synthase (AOS) knock-out mutants. As shown in FIG. 1, AOS has a particular importance in jasmonate biosynthesis, because the substrate for AOS also serves as the substrate for CYP74B in the C-6 volatile (FIG. 1). AOS catalyzes the dehydration of 13-(S)-hydroperoxylinolenic acid to 12,13-epoxylinolenic acid (allene oxide). AOS is a cytochrome P450 enzyme (CYP74A) encoded by a single copy gene in *Arabidopsis* (Laudert et al., 1996). CYP74A is a non-classical P450 in that it catalyzes in the absence of NADPH-dependent P450 reductase and oxygen (Schuler, (1996) *Crit Rev Plant Sci* 15:235–284). this phenomenon occurs only in the two members of the CYP74 family (Paquette et al. (2000) *DNA Cell Biol.* 19:307–317; Werck-Reichhart and Feyereisen (2000) *Genome Biology* 1:3001.3–3001.9). The CYP74 family members are also unusual among P450s in that they appear to contain chlorplast-targeting sequences (Paquette et al. (2000)).

FIG. 1 presents a diagram of jasmonic acid biosynthetic pathway schematically showing the following. Linolenic acid (18:3), which is released from membraned phospholipid by a lipase, is converted to the epoxy molecule allene oxide (12, 13-epoxy-octadecatrienoid acid) by a lipoxygenase (LOX) and allene oxide synthase, which is a member of the cytochrome p450 CYP74A family. One cyclization, one reduction, and three rounds of beta-oxidation steps are needed to generate the jasmonic acid which is the end product of the pathway from allene oxide.

The present invention reports the isolation of an AOS knock-out mutant (which cannot make endogenous JAs or its cyclopentenone precursors) by a PCR-based reverse genetics screening method (Winkler et al. (1998) *Plant Physiol.* 118:743–750). Biochemical analysis shows that internal level of jasmonic acid in the aos mutant is almost undetectable even after wound treatment. Characterization of the mutant phenotype shows that the aos mutant had a severe male sterility phenotype which did not recover during development but, which was rescued by exogenous MeJA spraying. Also, the aos mutant shows a defect in wound signal transduction in the *Arabidopsis* vegetative storage protein2 (AtVSP2) and lipoxygenase2 (AtLOX2) genes which are inducible by wound and JA treatments in the wild-type plant.

Thus, experiments performed in support of the present invention have shown the following. Mutation analysis of CYP74A mutants showed that plants bearing mutations at this locus showed severe male sterile symptoms due to defects of pollen and anther development. This male sterility was rescued by spraying the plants, at the flowering stage with jasmonic acid. In root development, the CYP74A mutants showed higher growth rates than wild-type. The wound and jasmonic acid responsive genes, such as vegetative storage protein-2 (VSP2), and lipoxygenase-2 (LOX2), were not induced in CYP74A mutants by wound treatment. These results suggest that jasmonic acid mediated wound signal transduction was interrupted in the mutants.

The activities of the CYP74A gene products are not dependent on either oxygen or NADPH, and it uses hydroperoxy fatty acids as substrates. Further, the gene products have an isoleucine in place of the typically conserved oxygen binding threonine at $327^{th}$ aa position in the translated CYP74A gene, which explains oxygen independency of the allene oxide synthase enzymes in the plant system. Further, CYP74A gene products have putative chloroplast targeting sequences.

The present invention relates to modulating the levels of the CYP74A gene products in plants. For example, by increasing expression of the CYP74A it may be possible to increase jasmonic acid production and decrease production of C6 volatiles. Manipulation of the levels of gene products produced by this gene (for example, by creation of overexpression mutants or deficient mutants) and analysis of the resulting molecular and physiological data will allow the elucidation of the relationship between jasmonic acid and C6 volatiles production. Further, by such manipulations of the levels of gene products the interaction between jasmonic acid and C6 volatiles signals in wound response can also be evaluated. The effects of such manipulations, by providing CYP74A mutant plants will also facilitate the analysis how such manipulations affect pathogen attack and insect feeding in the corresponding plants.

In one aspect of the present invention, a method is provided for producing F1 hybrid seed. In this method, plants blocked in the biosynthetic pathway for jasmonic acid (for example, plants defective in production of the CYP74A gene product) are male steriles. Addition of jasmonic acid at the flowering stage restores fertility to the male plants. This system is the most efficient approach for maintaining homozygous male sterile inbred plants that can be used for subsequent generation of commercial F1 hybrids.

Accordingly, the discoveries of the present invention relating to the roles of the gene products of the CYP74A gene represents important advancements in the understanding and regulation of plant reproduction and plant cell growth.

The polynucleotides and variations thereof described herein are therefore useful in the production of transgenic plants which display at least one of the above-described phenotypes related to altered expression of the CYP74A gene, so that the resulting plants have altered structure or morphology. The present invention particularly provides for altered structure or morphology such as altered flower and silique phenotypes and associated male sterility. Further, the CYP74A polypeptides can be expressed to engineer a plant with desirable properties. The engineering is accomplished by transforming plants with nucleic acid constructs described herein which may also comprise promoters (e.g., a promoter not normally associated with the gene that may lead to altered levels of expression) and/or altered coding sequences (such as deletions or point mutations). The transformed plants or their progenies are screened for plants that express the desired polypeptide.

Engineered plants exhibiting the desired altered structure or morphology can be used in plant breeding or directly in agricultural production or industrial applications, such as maintenance of homozygous male sterile inbred plants. Plants having the altered phenotypes can be crossed with other altered plants engineered with alterations in other growth modulation enzymes, proteins or polypeptides to produce lines with even further enhanced altered structural morphology characteristics compared to the parents or progenitor plants.

Although the following characterizations were carried out in *Arabidopsis*, the methods described herein can be applied to other plant species that comprises genes corresponding to the CYP74A gene described herein. Identification of homologs of these genes in other plants can be accomplished, for example, by sequence comparisons and/or hybridization screening with probes derived from these genes, wherein the probe selectively hybridizes with the gene of interest.

Figure 2:
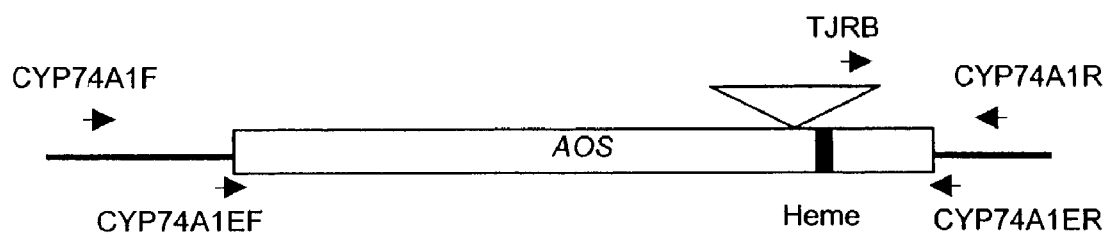
FIG. 2 schematically presents a map of the T-DNA mutagenized AOS gene. The AOS gene and flanking genomic regions, designated by open box and lines are shown, respectively. The heme binding domain of AOS gene is indiated by a closed box (Heme). Open triangles show the T-DNA insertion in the exon region of AOS gene. Closed arrows show locations and directions of primers used to screen aos mutant (CYP74A1F, CYP74A1R, and TJRB) and to clone the AOS exon region (CYP74A1EF, CYP74A1ER).

3. Characterization of Wild-Type CYP74A Expression and Phenotypes in Mutant Plants A number of mutants at the CYP74A locus have been identified in *Arabidopsis* using systemic reverse genetics (Example 1). A CYP74A mutant (designated CYP74A1-1) was isolated from TOM JACK lines (http://aims.cps.ms-u.edu/aims/). A second CYP74A mutant (designated CYP74A1-2) was isolated from Sussmann lines from the *Arabidopsis* Knock-Out facility ((http://www.biotech.wisc.edu/*Arabidopsis*/)). FIG. 2 shows the relative location of the T-DNA insert in the exon region of AOS gene as well as the heme binding site in this gene.

Further, co-segregation of the T-DNA insert with male sterility and chemical complementation of the male sterile phenotype in aos mutants with MeJA indicates that the male sterility in aos was caused by a disruption of AOS. (Example 4). However, to remove any possibility that the male sterile phenotype was caused by an unknown mutation, it was important to show that expression of AOS could complement the aos mutant phenotype. For functional complementation of the aos mutation, transgenic lines carrying AOS under the control of the cauliflower mosaic virus (CaMV) 35S promoter in wild-type plants were generated (see Materials and Methods).

Figure 3:
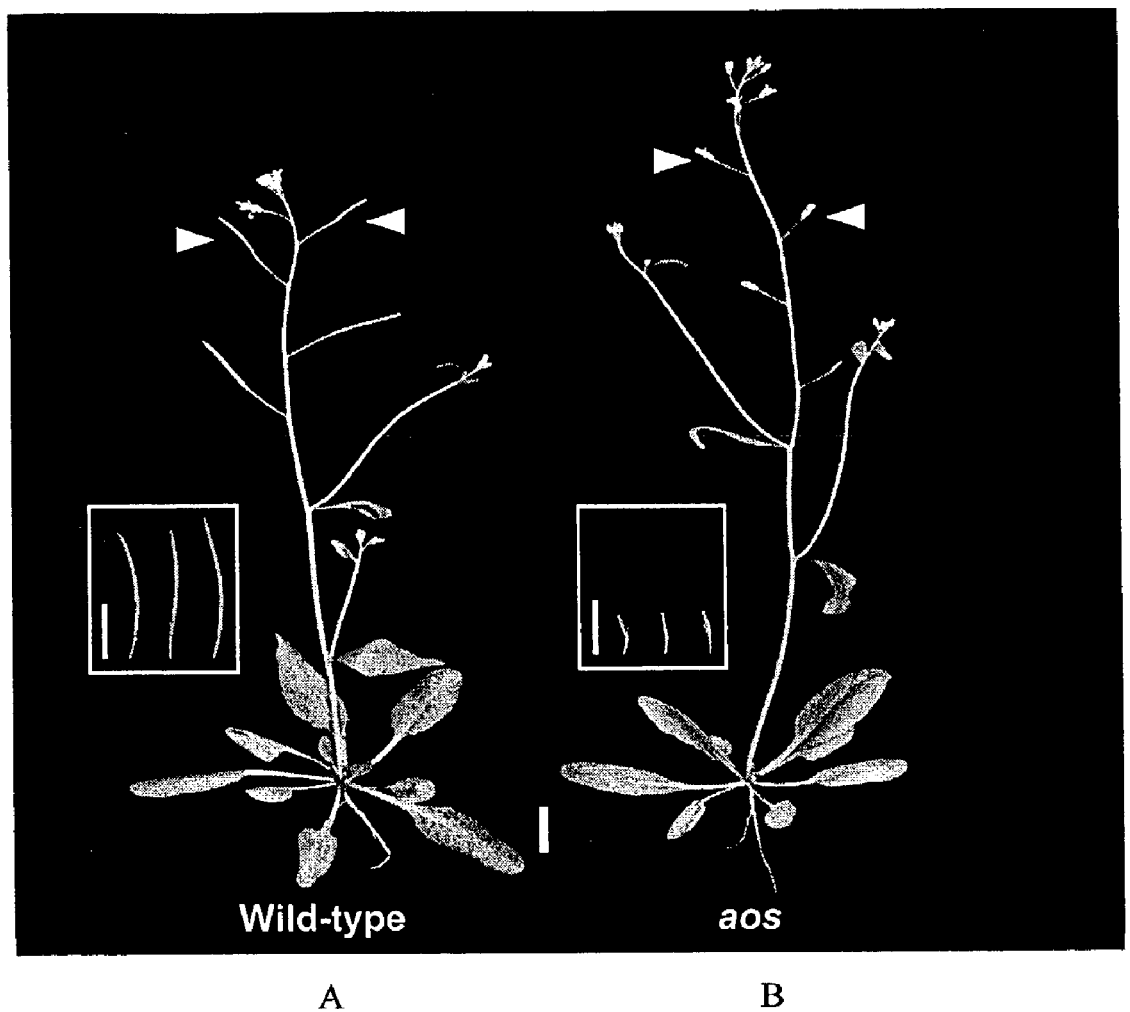
FIG. 3 is a reproduction of a photograph showing a representative comparison of *Arabidopsis thaliana* wild-type (Panel A) and aos mutant (Panel B) plants photographed 30 days after germination. The $3^{rd}$ and $4^{th}$ siliques of wild-type (left two open arrow heads) show normal development. Flowers of aos mutant (right two open arrow heads) fail to make siliques. The inset pictures show initial 3 siliques from the primary inflorescence of wild-type (left) and aos mutant (right) one week after flower opening, respectively. Bars=1 cM.

The plant phenotypes of *Arabidopsis thaliana* wild-type and CYP74A mutant plants were examined (Example 4). FIG. 3, Panels A and B present a photograph 30 days after germination of two representative plants. Flowers of CYP74A1-1 mutant fail to make siliques. This result is consistent with severe male sterile symptoms due to defects in anther and pollen production in CYP74A mutants.

Figure 4:
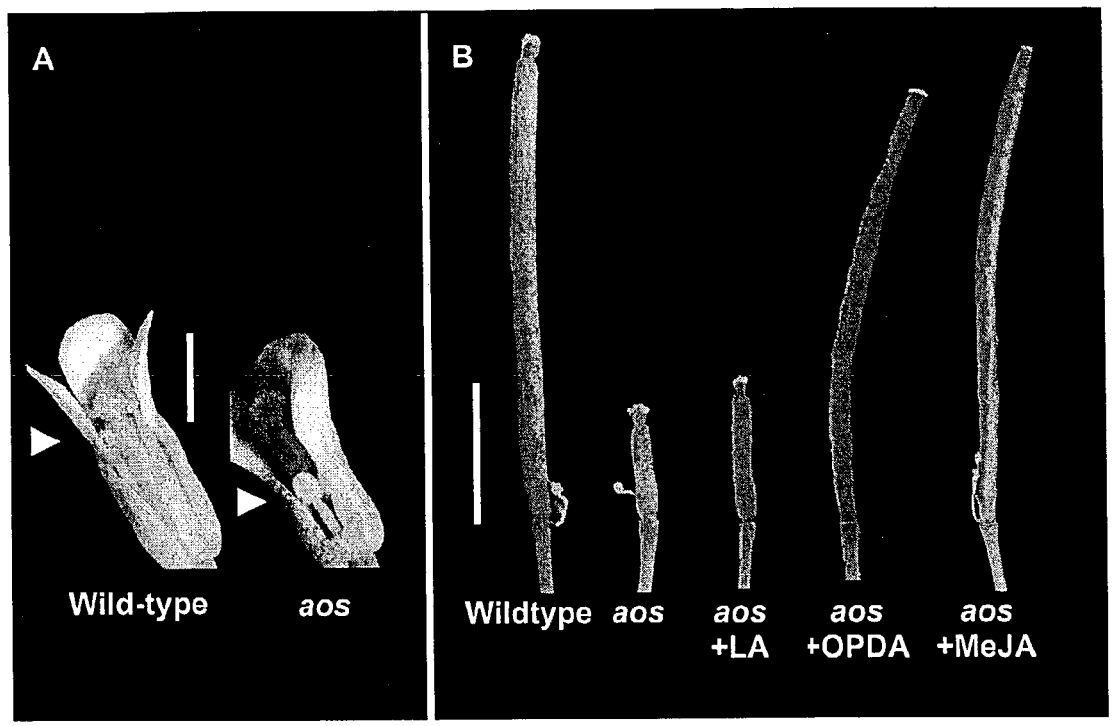
FIG. 4, Panels A and B, present half-tone reproductions of photographs showing recovery of fertility of aos mutant by exogenous methyl jasmonate spray. Panel (A) shows opened flowers of wild-type (left) and *Arabidopsis* aos mutant (right) were photographed. Anthers of the wild-type dehisced and pollens adhered on the stigmatic papilla (left open arrow head). The aos anthers were not fully elongated or dehisced yet (right open arrow head). Panel (B), shows (from the left) fully developed siliques of the wild-type, aos, and aos siliques treated with linolenic acid (LA), oxo-phytodienoic acid (OPDA) methyl-jasmonated (MeJA) were photographed two weeks after flower opening. Bars in (A)=1 mm and (B)=5 mm.

Experiments performed in support of the present invention indicated that exogenous application of jasmonic acid to plants bearing CYP74A mutations resulted in restoration of essentially wild-type siliques and recovered fertility in mutant plants (Example 4, FIG. 4, Panels A and B). Jasmonic acid is applied to the plants by spraying on the plant at flowering stage of development restores fertility to the male plants. In one aspect of the present invention, the use of exogenous application of jasmonic acid to CYP74A male sterile, mutant plants provides a system for maintaining homozygous male sterile inbred plants that can be used for subsequent generation of commercial F1 hybrids. For example, if a plant system, that bring very desirable traits, carries homozygous knock-out mutations in its ALLENE OXIDE SYNTHASEs, it can be used as a maternal parent to produce valuable F1 progenies with other preferred paternal parents without contaminated selfed progenies. This system can also be applied to all plant systems in which male fertility is at least partially dependent on the jasmonates.

Molecular analysis was also carried out to characterize the effects of CYP74A mutations. The results presented herein suggest that the CYP74A1-1 mutation is essentially a knock-out mutation of the CYP74A gene. Induction of jasmonates and jasmonic acid inducible genes by wound treatment was also examined in wild-type versus CYP74A mutant plants (Example 6). The results of these experiments indicated that the wound and jasmonic acid responsive genes, such as vegetative storage protein-2 (VSP2) and lipoxygenase-2 (LOX2), were not induced in the CYP74A1-1 mutant plants in response to wound treatment. These results suggest that jasmonic acid mediated wound signal transduction was interrupted in the mutant.

Figure 5:
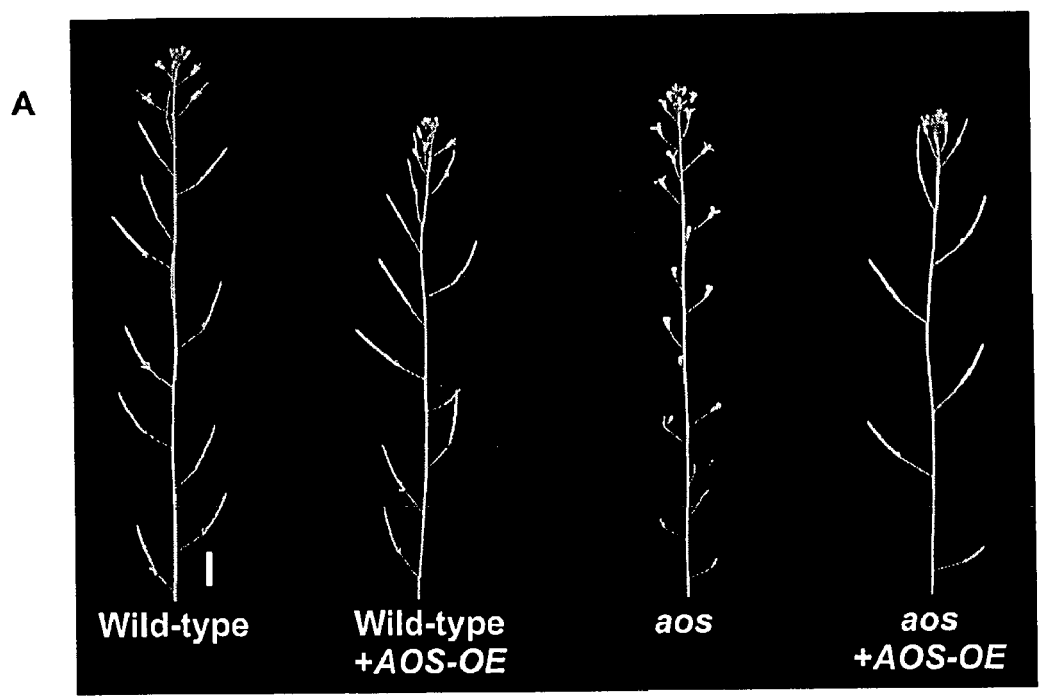
FIG. 5, panels A to C show the rescue of the male sterility phenotype in the of aos mutant with the constitutive AOS construct. Panel (A) shows (from the left), the primary inflorescence and siliques of wild-type, wild-type carrying the AOS-OE construct, aos, and a aos mutant carrying the AOS-OE construct were photographed 35 days after germination. Bar=1 cM. Panel (B) shows the AOS gene and flanking genomic regions (upper) and the AOS over-expression construct (AOS-OE) and flanking regions originated from pCAMBIA1300 (lower) are designated by open box and lines, respectively. The closed boxes were used to show the 35S promoter (P) and 35S poly(A) signal sequences (T) constructed in the over-expression construct. The open triangle shows the T-DNA insertion in the exon region of AOS gene (not drawn to scale). Closed arrows show locations and directions of primers for the genotyping which were used to identify genotypes of F2 progeny between aos and AOS-OE. The right border primer of the Tom Jack line and gene specific primer (upper; TJRB and CYP74A1R) were used to amplify the aos gene specific band. A set of gene specific primers was used to amplify the wild-type AOS gene specific band (middle; CYP74A1F2 and CYP74A1R). One gene specific primer and one plant binary vector (pCAMBIA1300) specific primer were used to amplify the over-expression construct specific bands (lower; CYP74A1F2 and pCAM1300F). Panel (C) depicts genotyping results of wild-type (far left), wild-type carrying AOS-OE (second from left), aos (second from right), and a aos mutant carrying the AOS-OE construct (far right), each tested for the presence of the AOS-, aos- or AOS-OE-specific PCR products.
Figure 5:
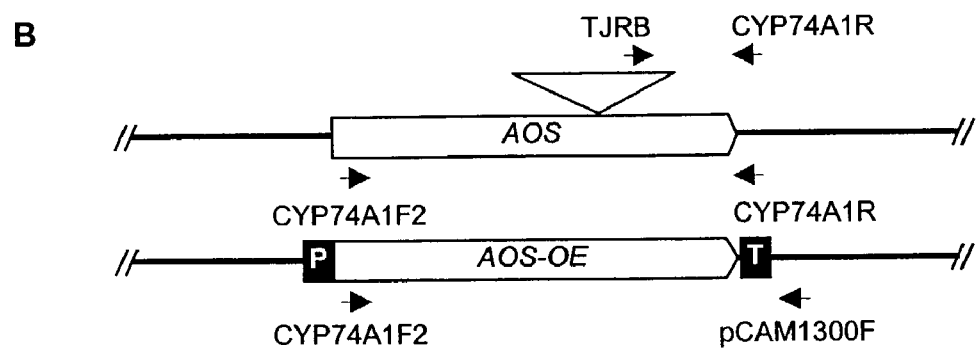
Figure 5:
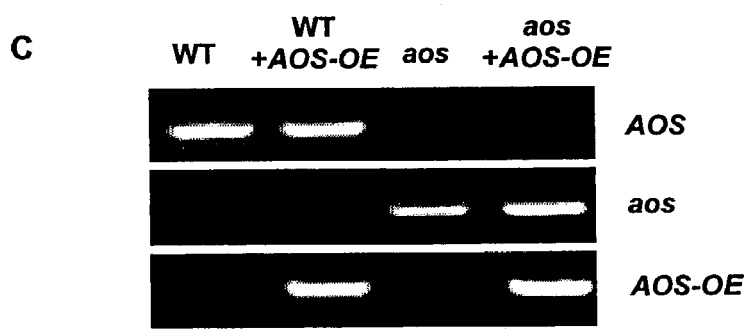

The effects of over-expression (relative to wild-type levels) of CYP74A in CYP74A mutant plants was also investigated (Example 5). FIG. 5, panels A–C indicate that constitutive expression of AOS rescues the male sterility phenotype in the aos mutant.

5. Isolation of Nucleic Acid Sequences from Plants

The isolation of CYP74A polynucleotides may be accomplished by a number of techniques. For instance, oligonucleotide probes based on the sequences disclosed herein can be used to identify the desired gene in a cDNA or genomic DNA library from a desired plant species. To construct genomic libraries, large segments of genomic DNA of the selected plant species are generated by random fragmentation, e.g. using restriction endonucleases, and are ligated with vector DNA to form concatemers that can be packaged into the appropriate vector. To prepare a library of tissue-specific cDNAs, mRNA is isolated from tissues and a cDNA library which contains the gene transcripts is prepared from the mRNA.

The cDNA or genomic library can then be screened using a probe based upon the sequence of a cloned gene such as the polynucleotides disclosed here. Probes may be used to hybridize with genomic DNA or cDNA sequences to isolate homologous genes in the same or different plant species. Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR.RTM and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying CYP74A genes from plant tissues are generated from comparisons of the sequences provided herein. For a general overview of PCR see Innis et al. eds, *PCR Protocols: A Guide to Methods and Applications*, Academic Press, San Diego (1990). Appropriate primers for this invention include, for instance, primers derived from the CYP74A polynucleotide sequences depicted in FIGS. 8 and 9, respectively. Suitable amplifications conditions may be readily determined by one of skill in the art in view of the teachings herein, for example, including reaction components and amplification conditions as follows: 10 mM Tris-HCl, pH 8.3, 50 mM potassium chloride, 1.5 mM magnesium chloride, 0.001% gelatin, 200 μM dATP, 200 μM dCTP, 200 μM dGTP, 200 μM dTTP, 0.4 μM primers, and 100 units per mL Taq polymerase; 96° C. for 3 min., 30 cycles of 96° C. for 45 seconds, 50° C. for 60 seconds, 72° C. for 60 seconds, followed by 72° C. for 5 min.

Polynucleotides may also be synthesized by well-known techniques as described in the technical literature. See, e.g., Carruthers, et al. (1982) *Cold Spring Harbor Symp. Quant. Biol.* 47:411–418, and Adams, et al. (1983) *J. Am. Chem. Soc.* 105:661. Double stranded DNA fragments may then be obtained either by synthesizing the complementary strand and annealing the strands together under appropriate conditions, or by adding the complementary strand using DNA polymerase with an appropriate primer sequence.

The polynucleotides of the present invention may also be used to isolate or create other mutant cell gene alleles. Mutagenesis consists primarily of site-directed mutagenesis followed by phenotypic testing of the altered gene product. Some of the more commonly employed site-directed mutagenesis protocols take advantage of vectors that can provide single stranded as well as double stranded DNA, as needed. Generally, the mutagenesis protocol with such vectors is as follows. A mutagenic primer, i.e., a primer complementary to the sequence to be changed, but consisting of one or a small number of altered, added, or deleted bases, is synthesized. The primer is extended in vitro by a DNA polymerase and, after some additional manipulations, the now double-stranded DNA is transfected into bacterial cells. Next, by a variety of methods, the desired mutated DNA is identified, and the desired protein is purified from clones containing the mutated sequence. For longer sequences, additional cloning steps are often required because long inserts (longer than 2 kilobases) are unstable in those vectors. Protocols are known to one skilled in the art and kits for site-directed mutagenesis are widely available from biotechnology supply companies, for example from Amersham Life Science, Inc. (Arlington Heights, Ill.) and Stratagene Cloning Systems (La Jolla, Calif.).

For example, wild-type CYP74A polynucleotide sequences in a selected plant of interest can be replaced by mutant CYP74A, e.g., deletions in the coding sequence or frame-shift mutations in the coding sequence, using homologous recombination for gene replacement. Also, knock-out technology using *Agrobacterium* mediated T-DNA insertion can be used to generate mutants carrying no functional CYP74A. Alternatively, over-expression mutant alleles could be introduced into a selected plant species as well. Such over-expression mutant alleles may be introduced into a plant of interest, for example, by gene replacement or by integration into other site(s) in the plant genome. Typically a selectable marker is included in the sequences being used for the gene replacement in order to facilitate screening.

6. Control Elements

Regulatory regions can be isolated from the CYP74A gene locus and used in recombinant constructs for modulating the expression of the gene or a heterologous gene in vitro and/or in vivo. This region may be used in its entirety or fragments of the region may be isolated which provide the ability to direct expression of a coding sequence linked thereto.

Thus, promoters can be identified by analyzing the 5' sequences of a genomic clone including the CYP74A gene and sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. (See, J. Messing et al., in *Genetic Engineering in Plants*, pp. 221–227 (Kosage, Meredith and Hollaender, eds. (1983)). Methods for identifying and characterizing promoter regions in plant genomic DNA are described, for example, in Jordano et al. (1989) *Plant Cell* 1:855–866; Bustos et al (1989) *Plant Cell* 1:839–854; Green et al. (1988) *EMBO J.* 7:4035–4044; Meier et al. (1991) *Plant Cell* 3:309–316; and Zhang et al (1996) *Plant Physiology* 110:1069–1079).

Additionally, the promoter region may include nucleotide substitutions, insertions or deletions that do not substantially affect the binding of relevant DNA binding proteins and hence the promoter function. It may, at times, be desirable to decrease the binding of relevant DNA binding proteins to "silence" or "down-regulate" a promoter, or conversely to increase the binding of relevant DNA binding proteins to "enhance" or "up-regulate" a promoter. In such instances, the nucleotide sequence of the promoter region may be modified by, e.g., inserting additional nucleotides, changing the identity of relevant nucleotides, including use of chemically-modified bases, or by deleting one or more nucleotides.

Promoter function can be assayed by methods known in the art, preferably by measuring activity of a reporter gene operatively linked to the sequence being tested for promoter function. Examples of reporter genes include those encoding luciferase, green fluorescent protein, GUS, neo, cat and bar.

Polynucleotides comprising untranslated (UTR) sequences and intron/exon junctions may also be identified. UTR sequences include introns and 5' or 3' untranslated regions (5' UTRs or 3' UTRs). These portions of the gene, especially UTRs, can have regulatory functions related to, for example, translation rate and mRNA stability. Thus, these portions of the gene can be isolated for use as elements of gene constructs for expression of polynucleotides encoding desired polypeptides.

Introns of genomic DNA segments may also have regulatory functions. Sometimes promoter elements, especially transcription enhancer or suppressor elements, are found within introns. Also, elements related to stability of heteronuclear RNA and efficiency of transport to the cytoplasm for translation can be found in intron elements. Thus, these segments can also find use as elements of expression vectors intended for use to transform plants.

The introns, UTR sequences and intron/exon junctions can vary from the native sequence. Such changes from those sequences preferably will not affect the regulatory activity of the UTRs or intron or intron/exon junction sequences on expression, transcription, or translation. However, in some instances, down-regulation of such activity may be desired to modulate traits or phenotypic or in vitro activity.

7. Use of Nucleic Acids of the Invention to Inhibit Gene Expression

The isolated sequences prepared as described herein, can be used to prepare expression cassettes useful in a number of techniques. For example, expression cassettes of the invention can be used to suppress (under-express) endogenous CYP74A gene expression. Inhibiting expression can be useful, for instance, in producing a male sterile phenotype, as described above. Further, the inhibitory polynucleotides of the present invention can also be used in combination with over-expressing constructs described below, for example, using suitable tissue-specific promoters linked to polynucleotides described herein. In this way, the polynucleotides can be used to modulate phenotypes in selected tissue and, at the same time, modulate phenotypes in different tissue(s).

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, antisense RNA may inhibit gene expression by preventing the accumulation of mRNA which encodes the enzyme of interest, see, e.g., Sheehy et al (1988) *Proc. Nat. Acad. Sci. USA* 85:8805–8809, and Hiatt et al., U.S. Pat. No. 4,801,340.

The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred. It is to be understood that any integer between the above-recited ranges is intended to be captured herein.

Catalytic RNA molecules or ribozymes can also be used to inhibit expression of CYP74A gene. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al (1988) *Nature* 334:585–591.

Another method of suppression is sense suppression. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al (1990) *The Plant Cell* 2:279–289 and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 50%–65%, but a higher identity might exert a more effective repression of expression of the endogenous sequences. Substantially greater identity of more than about 80% is preferred, though about 95% to absolute identity would be most preferred. It is to be understood that any integer between the above-recited ranges is intended to be captured herein. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants which are over-expressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

8. Use of Nucleic Acids of the Invention to Enhance Gene Expression

The present invention may also be used to over-express CYP74A. For example, by operably linking the CYP74A coding sequence to a promoter which allows for over-expression of the gene. (See the discussion regarding promoters below. See also, Example 7) The exogenous CYP74A polynucleotides do not have to code for exact copies of the endogenous CYP74A proteins. Modified protein chains can also be readily designed utilizing various recombinant DNA techniques well known to those skilled in the art and described for instance, in Sambrook et al., supra. Hydroxylamine can also be used to introduce single base mutations into the coding region of the gene (Sikorski et al (1991) *Meth. Enzymol.* 194: 302–318). For example, the chains can vary from the naturally occurring sequence at the primary structure level by amino acid substitutions, additions, deletions, and the like. These modifications can be used in a number of combinations to produce the final modified protein chain.

It will be apparent that the polynucleotides described herein can be used in a variety of combinations. For example, the polynucleotides can be used to produce different phenotypes in the same organism, for instance by using tissue-specific promoters to over-express a CYP74A polynucleotide in certain tissues (e.g., leaf tissue) while at the same time using tissue-specific promoters to inhibit expression of in other tissues. In addition, fusion proteins of the polynucleotides described herein with other known polynucleotides (e.g., polynucleotides encoding products involved in the brassinosteroid pathway) can be constructed and employed to obtain desired phenotypes.

Any of the polynucleotides described herein can also be used in standard diagnostic assays, for example, in assays for mRNA levels (see, Sambrook et al, supra); as hybridization probes, e.g., in combination with appropriate means, such as a label, for detecting hybridization (see, Sambrook et al., supra); as primers, e.g., for PCR (see, Sambrook et al., supra); attached to solid phase supports and the like.

9. Preparation of Recombinant Vectors

To use isolated sequences in the above techniques, recombinant DNA vectors suitable for transformation of plant cells are prepared. Techniques for transforming a wide variety of higher plant species are well known and described further below as well as in the technical and scientific literature. See, for example, Weising et al (1988) *Ann. Rev. Genet.* 22:421–477. A DNA sequence coding for the desired polypeptide, for example a cDNA sequence encoding full-length CYP74A protein, will preferably be combined with transcriptional and translational initiation regulatory sequences which will direct the transcription of the sequence from the gene in the intended tissues of the transgenic plant.

Such regulatory elements include but are not limited to the promoters derived from the genome of plant cells (e.g., heat shock promoters such as soybean hsp17.5-E or hsp17.3-B (Gurley et al. (1986) *Mol. Cell. Biol.* 6:559–565); the promoter for the small subunit of RUBISCO (Coruzzi et al. (1984) *EMBO J.* 3:1671–1680; Broglie et al (1984) *Science* 224:838–843); the promoter for the chlorophyll a/b binding protein) or from plant viruses viral promoters such as the 35S RNA and 19S RNA promoters of CaMV (Brisson et al. (1984) *Nature* 310:511–514), or the coat protein promoter of TMV (Takamatsu et al. (1987) *EMBO J.* 6:307–311), cytomegalovirus hCMV immediate early gene, the early or late promoters of SV40 adenovirus, the lac system, the trp system, the TAC system, the TRC system, the major operator and promoter regions of phage λ, the control regions of fd coat protein, the promoter for 3-phosphoglycerate kinase, the promoters of acid phosphatase, heat shock promoters (e.g., as described above) and the promoters of the yeast alpha-mating factors.

In construction of recombinant expression cassettes of the invention, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the T-DNA mannopine synthetase promoter (e.g., the 1'- or 2'-promoter derived from T-DNA of *Agrobacterium tumafaciens*), and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers such as tissue- or developmental-specific promoter, such as, but not limited to the CHS promoter, the PATATIN promoter, etc. The tissue specific E8 promoter from tomato is particularly useful for directing gene expression so that a desired gene product is located in fruits.

Other suitable promoters include those from genes encoding embryonic storage proteins. Examples of environmental conditions that may affect transcription by inducible promoters include anaerobic conditions, elevated temperature, or the presence of light. If proper polypeptide expression is desired, a polyadenylation region at the 3'-end of the coding region should be included. The polyadenylation region can be derived from the natural gene, from a variety of other plant genes, or from T-DNA. In addition, the promoter itself can be derived from the CYP74A gene, as described above.

The vector comprising the sequences (e.g., promoters or coding regions) from CYP74A will typically comprise a marker or reporter gene which confers a selectable or detectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta, or the reporter may produce a detectable signal, such as light-generation produced via a luciferase encoding gene or a flourescent protein encoding gene.

10. Production of Transgenic Plants

DNA constructs may be introduced into the genome of the desired plant host by a variety of conventional techniques. For reviews of such techniques see, for example, Weissbach & Weissbach *Methods for Plant Molecular Biology* (1988, Academic Press, N.Y.) Section VIII, pp. 421–463; and Grierson & Corey, *Plant Molecular Biology* (1988, 2d Ed.), Blackie, London, Ch. 7–9. For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al (1987) *Nature* 327:70–73). Alternatively, the DNA constructs may be combined with suitable T-DNA flanking regions and introduced into a conventional *Agro-*

*bacterium tumefaciens* host vector. *Agrobacterium tumefaciens*-mediated transformation techniques, including disarming and use of binary vectors, are well described in the scientific literature. See, for example Horsch et al (1984) *Science* 233:496–498, and Fraley et al (1983) *Proc. Nat'l. Acad. Sci. USA* 80:4803. The virulence functions of the *Agrobacterium tumefaciens* host will direct the insertion of the construct and adjacent marker into the plant cell DNA when the cell is infected by the bacteria using binary T DNA vector (Bevan (1984) *Nuc. Acid Res.* 12:8711–8721) or the co-cultivation procedure (Horsch et al (1985) *Science* 227: 1229–1231). Generally, the *Agrobacterium* transformation system is used to engineer dicotyledonous plants (Bevan et al (1982) *Ann. Rev. Genet* 16:357–384; Rogers et al (1986) *Methods Enzymol.* 118:627–641). The *Agrobacterium* transformation system may also be used to transform, as well as transfer, DNA to monocotyledonous plants and plant cells. (see Hernalsteen et al (1984) *EMBO J* 3:3039–3041; Hooykass-Van Slogteren et al (1984) *Nature* 311:763–764; Grimsley et al (1987) *Nature* 325:1677–179; Boulton et al (1989) *Plant Mol. Biol.* 12:31–40.; and Gould et al (1991) *Plant Physiol.* 95:426–434).

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717–2722, Potrykus et al. (1985) *Molec. Gen. Genet.* 199:169–177; Fromm et al. (1985) *Proc. Nat. Acad. Sci. USA* 82:5824–5828; and Shimamoto (1989) *Nature* 338:274–276) and electroporation of plant tissues (D'Halluin et al. (1992) *Plant Cell* 4:1495–1505). Additional methods for plant cell transformation include microinjection, silicon carbide mediated DNA uptake (Kaeppler et al. (1990) *Plant Cell Reporter* 9:415–418), and microprojectile bombardment (see Klein et al. (1988) *Proc. Nat. Acad. Sci. USA* 85:4305–4309; and Gordon-Kamm et al. (1990) *Plant Cell* 2:603–618).

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in Handbook of Plant Cell Culture, pp. 124–176, Macmillian Publishing Company, New York, 1983; and Binding, *Regeneration of Plants, Plant Protoplasts*, pp. 21–73, CRC Press, Boca Raton, 1985. Regeneration can also be obtained from plant callus, explants, organs, pollens, embryos or parts thereof. Such regeneration techniques are described generally in Klee et al (1987) *Ann. Rev. of Plant Phys.* 38:467–486.

The nucleic acids of the invention can be used to confer desired traits on essentially any plant. A wide variety of plants and plant cell systems may be engineered for the desired physiological and agronomic characteristics described herein using the nucleic acid constructs of the present invention and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the invention has use over a broad range of plants, including, but not limited to, species from the genera *Asparagus, Avena, Brassica, Citrus, Citrullus, Capsicum, Cucurbita, Daucus, Glycine, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna*, and *Zea*.

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection may be performed by growing the engineered plant material on media containing an inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or Cl genes) that may be present on the recombinant nucleic acid constructs of the present invention. Such selection and screening methodologies are well known to those skilled in the art.

Physical and biochemical methods also may be used to identify plant or plant cell transformants containing the gene constructs of the present invention. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods of this invention can be observed by, for example, northern blots of the RNA (e.g., mRNA) isolated from the tissues of interest. Typically, if the amount of mRNA has increased, it can be assumed that the endogenous CYP74A gene is being expressed at a greater rate than before. Other methods of measuring CYP74A activity can be used. For example, segregation of the male sterile phenotype of CYP74A mutant alleles can be followed, or the inability to produce jasmonic acid. Such assays are known in the art (see, for example, Example 6). Different types of enzymatic assays can be used, depending on the substrate used and the method of detecting the increase or decrease of a reaction product or by-product. In addition, the levels of CYP74A protein expressed can be measured immunochemically, i.e., ELISA, RIA, EIA and other antibody based assays well known to those of skill in the art, such as by electrophoretic detection assays (either with staining or western blotting).

The transgene may be selectively expressed in some tissues of the plant or at some developmental stages, or the transgene may be expressed in substantially all plant tissues, substantially along its entire life cycle. However, any combinatorial expression mode is also applicable.

The present invention also encompasses seeds of the transgenic plants described above wherein the seed has the transgene or gene construct. The present invention further encompasses the progeny, clones, cell lines or cells of the transgenic plants described above wherein said progeny, clone, cell line or cell has the transgene or gene construct.

11. Polypeptides

The present invention also includes CYP74A polypeptides, including such polypeptides as a fusion, or chimeric protein product (comprising the protein, fragment, analogue, mutant or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art.

A CYP74A analog, whether a derivative, fragment or fusion of native CYP74A polypeptides, is capable of at least one CYP74A activity. Preferably, the analogs exhibit at least 60% of the activity of the native protein, more preferably at least 70% and even more preferably at least 80%, 85%, 90% or 95% of at least one activity of the native protein.

Further, such analogs exhibit some sequence identity to the native CYP74A polypeptide sequence. Preferably, the variants will exhibit at least 35%, more preferably at least 59%, even more preferably 75% or 80% sequence identity, even more preferably 85% sequence identity, even more preferably, at least 90% sequence identity; more preferably at least 95%, 96%, 97%, 98% or 99% sequence identity.

CYP74A analogs can include derivatives with increased or decreased activities as compared to the native CYP74A polypeptides. Such derivatives can include changes within the domains, motifs and/or consensus regions of the native CYP74A polypeptide.

One class of analogs is those polypeptide sequences that differ from the native CYP74A polypeptide by changes, insertions, deletions, or substitution; at positions flanking the domain and/or conserved residues. For example, an analog can comprise (1) the domains of a CYP74A polypeptide and/or (2) at conserved or nonconserved residues. For example, an analog can comprise residues conserved between the CYP74A polypeptide and other cytochrome P450 proteins with other regions of the molecule changed.

Another class of analogs includes those that comprise a CYP74A polypeptide sequence that differs from the native sequence in the domain of interest or conserved residues by a conservative substitution.

Yet another class of analogs includes those that lack one of the in vitro activities or structural features of the native CYP74A polypeptides, for example, dominant negative mutants or analogs that comprise a heme-binding domain but other inactivated domains.

CYP74A polypeptide fragments can comprise sequences from the native or analog sequences, for example fragments comprising one or more of the following P450 domains or regions: A, B, C, D, anchor binding, and proline rich. Such domains and regions are known.

Fusion polypeptides comprising CYP74A polypeptides (e.g., native, analogs, or fragments thereof) can also be constructed. Non-limiting examples of other polypeptides that can be used in fusion proteins include chimeras of CYP74A polypeptides and fragments thereof; and other known P450 polypeptides or fragments thereof.

In addition, CYP74A polypeptides, derivatives (including fragments and chimeric proteins), mutants and analogues can be chemically synthesized. See, e.g., Clark-Lewis et al. (1991) *Biochem.* 30:3128–3135 and Merrifield (1963) *J. Amer. Chem. Soc.* 85:2149–2156. For example, CYP74A, derivatives, mutants and analogues can be synthesized by solid phase techniques, cleaved from the resin, and purified by preparative high performance liquid chromatography (e.g., see Creighton, 1983, Proteins, Structures and Molecular Principles, W. H. Freeman and Co., N.Y., pp. 50–60). CYP74A, derivatives and analogues that are proteins can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49).

Further, the polynucleotides and polypeptides described herein can be used to generate antibodies that specifically recognize and bind to the protein products of the CYP74A polynucleotides. (See, Harlow and Lane, eds. (1988) "Antibodies: A Laboratory Manual"). The polypeptides and antibodies thereto can also be used in standard diagnostic assays, for example, radioimmunoassays, ELISA (enzyme linked immunoradiometric assays), "sandwich" immunoassays, immunoradiometric assays, in situ immunoassay, western blot analysis, immunoprecipitation assays, immunofluorescent assays and PAGE-SDS.

12. Applications

The present invention finds use in various applications, for example, including but not limited to those listed above. In particular, the present invention contemplates production of transgenic plants that over or under-express CYP74A, thereby producing any of the various phenotypes specified above. Thus, the CYP74A polynucleotides may be placed in recombinant vectors which may be inserted into host cells to express the CYP74A protein, under the control of promoters that either enhance or decrease CYP74A expression.

The nucleic acid molecules may be used to design plant CYP74A antisense molecules, useful, for example, in plant CYP74A gene regulation or as antisense primers in amplification reactions of plant gene nucleic acid sequences. With respect to plant gene regulation, such techniques can be used to regulate, for example, plant growth, development or gene expression. Further, such sequences may be used as part of ribozyme and/or triple helix sequences, also useful for gene regulation.

Thus, the molecules of the present invention can be used to provide male sterile plants (e.g., CYP74A mutants) with a reversible phenotype (e.g., by application of jasmonic acid at the flowering stage). The *Arabidopsis* CYP74A protein can be used in any biochemical applications (experimental or industrial), for example, but not limited to, regulation of jasmonic acid synthesis and/or C6 volatiles, modification of reproductive function, and experimental or industrial biochemical applications known to those skilled in the art.

13. Application of Exogenous Substances

In certain aspects, the invention includes applying one or more exogenous substances to plants to alleviate male sterility. Thus, in preferred embodiments, the plant comprises a mutant in the aos gene, for example, a knock-out mutant and the exogenous substance comprises a substance involved in production of jasmonic acid, for example, jasmonic acid or derivatives thereof (e.g, methyl ester of jasmonic acid (MeJA)), linolenic acid (LA), and/or oxo-phytodienoic acid (OPDA). The exogenous substance can be administered using any suitable delivery technique including but not limited to spraying, coating, dipping, powdering and the like. Single or multiple application regimes can be used, for example, treatment twice a day over a period of 1 day, 2 days, 1 week or longer. The concentration of exogenous substance(s) useful in relieving the male sterility phenotype can be readily determined by the teachings herein. For example, in certain embodiments, the exogenous substance comprises between 0.1% and 50% of a solution, more preferably between about 0.5% and 15% of a solution, more preferably between about 0.5% and 5% and even more preferably around 1% of a solution. In other embodiments, the exogenous substance is applied at a concentration of between about 0.1 and 50 mM, more preferably between about 0.5 and 25 mM, more preferably between about 1 and 10 mM, and even more preferably between about 1 and 5 mM.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Mutant Isolation

To isolate *Arabidopsis thaliana* aos mutants, we screened T-DNA mutagenized *Arabidopsis* lines generated by Tom Jack (TJ; ecotype Col-6; 6,000 lines), Ken Feldmann (KF; ecotype Wassilewskija [Ws-2]; 6,000 lines) and the *Arabidopsis* knockout facility (AKF; http://www.biotech.wisc.edu/*Arabidopsis*/; ecotype Ws-2; 60,750 lines) by reverse genetics using combinations of gene and T-DNA border specific primers (Winkler et al., 1998).

Based on the sequence of wild-type genomic DNA, a pair of gene specific primers (CYP74A1F, 5'-AACATATGCT-CAAGGGATGGAGCTAAAAG-3' (SEQ ID NO:3) and CYP74A1R, 5'-CGAACATGTAGAGCAGCAACTGAT-TATACA-3' (SEQ ID NO:4)) were designed to screen mutants. TJLB (5'-CTTTCGCCTATAAATACGACG-GATCGTA-3' (SEQ ID NO:5) and TJRB (5'-CGGGC-CTAACTTTTGGTGTGATGATGCT-3' (SEQ ID NO:6)) primers for TJ lines, KFLB (5'-GATGCACTCGAAAT-CAGCCAATTTTAGAC-3' (SEQ ID NO:7)) and KFRB (5'-TCCTTCAATCGTTGCGGTTCTGTCAGTTC-3' (SEQ ID NO:8)) primers for KF lines, and JL202 (5'-CATTT-TATAATAACGCTGCGGACATCTAC-3' (SEQ ID NO:9)) and JL270 (5'-TTTCTCCATATTGACCATCATACT-CATTG-3' (SEQ ID NO:10)) primers for AKF lines were used as T-DNA border primers. To amplify the regions flanking the T-DNA insertion, CYP74A1F and CYP74A1R primers were used. After primary screening of super-pools by PCR, using combinations of these gene and border specific primers, amplified bands were blotted on a nylon membrane (Roche, USA) and probed by a DIG (digoxygenin)-labeled AOS gene specific probe to identify and positive super-pools. The preparation of the DIG-labeled probe and Southern blot analysis were performed using a DIG DNA Labeling and Detection Kit (Roche, USA). After the second round of screening corresponding sub-pools, amplified DNA fragments were purified using Qiaquick colunms (Qiagen Inc., USA) and sequenced with the border primer, to identify the T-DNA insertion site in the AOS. From this screening, a aos knock-out mutant was found in TJ line 1180 which is available through the *Arabidopsis* Biological Resource Center (ABRC) seed catalog (http://aims.cps.msu.edu/aims).

Plant Growth Condition and Wound Treatment

*Arabidopsis thaliana* wild-type (Col-6) and aos mutant seeds were sown on 7 cm round pots containing Metro-Mix 350 (Scotts, USA) and cold treated at 4° C. for 3 days. After cold treatment, plants were incubated in a controlled growth room under long day conditions (16 h of light at 22° C./8 h of dark at 20° C.).

For wound treatments, all but the $1^{st}$ and $2^{nd}$ rosette leaves of 4 week old plants were crushed several times across the mid-vein with laminated forceps, which effectively wounded 40%~50% of the leaf area. Plants were incubated for 0, 2, 4, and 8 hours, after which the leaves were harvested and immediately frozen in liquid nitrogen. The 0 h time point indicates harvests of leaves from unwounded control plants. For over-expression lines, wounded leaves were harvested and frozen at 0, 0.5, 1, 2, 4, and 8 hours after wound treatment.

Jasmonate Measurement and Chemical Treatments

The four youngest fully developed leaves of 4-weeks old plants (4 per treatment) were wounded with a pattern wheel producing 3 rows of puncture wounds on each leaf half. The treated leaves were harvested at the indicated time points (0.5; 1; 2; 4; 8; 24; and 48 h) and immediately frozen in liquid nitrogen. The 0 h time point indicates harvests of leaves from unwounded control plants. The samples were analyzed by GC-MS after addition of 172 ng of $^{13}C_{1,2}$-JA as an internal standard and sample preparation as described by Schittko et al. (2000) *Planta* 210:343–346 with the following modifications of the extraction procedure. Leaf samples were homogenized in the extraction buffer by utilizing the FastPrep extraction system FP120 (Savant Instruments, Holbrook, N.Y.). Tissue was homogenized by reciprocating shaking at 6.0 m sec$^{-1}$ for 90 sec in extraction tubes containing 900 mg of lysing matrix (BIO 101, Vista, Calif.).

Application of linolenic acid (LA; Cayman Chemical, USA) and methyl jasmonate (MeJA; Sigma-Aldrich, USA) to recover male sterility of *Arabidopsis* aos mutant was done by spraying 1% of LA and 2 mM MeJA directly on *Arabidopsis* flower buds of 4 week old plants grown under long day condition. Oxo-phytodienoic acid (OPDA; Cayman Chemical, USA) was applied by dipping of floral buds in the 1 mM OPDA and 0.01% TritonX-100 (Sigma-Aldrich, USA) solution. These plants were sprayed twice a day for two days. The plants were monitored for silique production over the next two weeks.

Extraction of RNA and RT-PCR Analysis

Total RNA of frozen tissues was extracted with Trizol (Sigma-Aldrich, USA). After RNase free DNase treatment, one µg of total RNA was used to make first strand cDNA using the SuperScript II RNase H$^-$ Reverse Transcriptase (Life Technology, USA).

To analyze wound-induced expression levels of *Arabidopsis thaliana* vegetative storage protein2 (AtVSP2), lipoxygenase2 (AtLOX2) and AOS genes, RT-PCR analyses were performed using the first strand cDNAs as templates. CYP74A1EF/CYP74A1ER, ATVSP2F (5'-ACATCAC-GAATTCAACAATAAACCATACCAT-3' (SEQ ID NO:11))/ATVSP2R (5'-GGAGAATTCGATGAAGATA-GATTCTTAAGAA-3' (SEQ ID NO:12)), and ATLOX2F (5'-TTGGCTGAGGAAGATAAGACCGCAGAACAT-3' (SEQ ID NO:13))/ATLOX2R (5'-TCATTTTATCAAGAA-GACAGAGATACAGAA-3' (SEQ ID NO:14)) primer sets were used as specific primers of AOS, AtVSP2, and ALOX2 genes, respectively. The conditions for PCR amplification were as follows: denature samples at 95° C. for 3 min and then 30 cycles at 94° C. for 30 sec, 58° C. for 30 sec, and 72° C. for 2 min. For use as a positive control, the Arabidopsis ACTIN-2 gene was amplified under the same conditions with the following two primers: ACT2F (5'-ACAT-CACGAATTCAACAATAAACCATACCAT-3' (SEQ ID NO:11)) and ACT2R (5'-GGAGAATTCGATGAAGATA-GATTCTTAAGAA-3' (SEQ ID NO:12)).

Isolation of AOS Over-Expression Lines

The wild-type Arabidopsis AOS gene was amplified with CYP74A1EF (5'-CCATATTCT AGATCACAACACTCGCCACTG-3' (SEQ ID NO:15)) and CYP74A1ER (5'-CAGATT CTAGAACATTTTCTCAAAATTCACG-3 (SEQ ID NO:16)) primers (underlined letter show modified sequences for cloning by enzyme digestion). The amplified AOS gene was digested with XbaI and cloned into XbaI digested pUC19 vectors. The cloned Arabidopsis genes were sequenced with CYP74A1EF and CYP74A1ER. To complete sequencing of the cloned AOS gene, CYP74A1EF2 (5'-GGAGCCTAAACACGAAAAGCTC-3' (SEQ ID NO:17)) and CYP74A1ER2 (5'-TTAACTC-CATTTTCTCAATCGC-3' (SEQ ID NO:18)) primers were designed. The cloned Arabidopsis AOS gene was isolated by SalI and XbaI double digestion and cloned into XhoI and XbaI digested pRT101 vectors containing the 35S promoter and the polyadenylation signal (Reinhard Töfer, et al., 1987). Then, the over-expression construct including the 35S promoter and polyadenylation signal of the CAMV and the Arabidopsis AOS gene was isolated by digestion with PstI and ligated into the PstI site of Agrobacterium binary vector pCAMBIA1300 (AF234296). The construct was transformed initially into Agrobacterium strain GV3101 by electroporation and then into the wild-type Arabidopsis ecotype Col-6 by the floral dip method (Clough and Bent (1998) Plant J. 16:735–743).

Seeds collected from the transformed plants were surface-sterilized with 30% bleach and 0.01% Triton X-100 (Sigma, USA) for 10 min, and washed five times with sterile distilled water. After surface-sterilization, seeds were plated on 0.8% agar-solidified medium containing Murashige-Skoog (MS) salts (GIBCO-BRL, USA) supplemented with 2% sucrose and 50 mg/L hygromycin-B (Life Technology, USA) and stored at 4° C. for three days. After vernalization, the seeds were transferred to long day conditions (16 h light [with a minimum intensity of 100 μmolm$^{-2}$s$^{-1}$] at 22° C./8 h dark at 20°C.). Ten independent hygromycin resistant T1 seedlings were transferred to soil and segregating T2 seeds were harvested. To isolate homozygous lines for the over-expression construct, six border specific primers (pCAMTAIL1L, 5'-CAATACGAGGTCGCCAACATCTTCTTCT-3' (SEQ ID NO:19); pCAMTAIL2L, 5'-CAACTCTATCAGAGCT-TGGTTGACGGCA-3' (SEQ ID NO:20); pCAMTAIL3L, 5'-CTGTGTAGAAGTACTCGCCGATAGTGGAAA-3' (SEQ ID NO:21); pCAMTAIL1R, 5'-CACTGGC-CGTCGTTTTACAACGTCGTGA-3' (SEQ ID NO:22); pCAMTAIL2R, 5'-GCACCGATCGCCCTTCCCAA-CAGTT-3' (SEQ ID NO:23); pCAMTAIL3R, 5'-CAGAT-TGTCGTTTCCCGCCTTCAGTTTA-3' (SEQ ID NO:24)) were designed and flanking regions of over-expression constructs were amplified by thermal asymmetric interlaced (TAIL)-PCR (Liu et al. (1995) Plant J. 8:457–463). Based on sequences of the flanking region, specific primers were designed and the genotypes of T2 families were examined. Three independent homozygous lines were chosen for measurement of internal and wound induced JA accumulation.

Complementation Analysis

For complementation analysis, aos mutants were crossed to AOS over-expression lines. Three independent AOS over-expression plants were used as pollen donors to cross to aos mutants. The F2 segregating lines from these crosses were examined by PCR to identify genotypes of segregating F2 plants. Two AOS specific primers, CYP74A1F2 (5'-GTAC-GATCAAAGCCGTTGAAATTCCGAGTTTT-3' (SEQ ID NO:25)) and CYP74A1R2 (5'-TGGAACAAGAAAACA-GATGGACTACACAGGT-3' (SEQ ID NO:26)) and a pCAMBIA1300 specific primer, pCAM1300F (5'-CTCATT-AGGCACCCCAGGCTTTACACTT-3' (SEO ID NO:27)) were designed. Twenty four kanamycin and hygromycin resistant plants for each independent F2 families were selected and transferred to soil and grown in the under long days as described. For the genotyping of F2 plants, genomic DNA was isolated from one rosette leaf per plant with 500 μl of extraction buffer (0.2 M Tris.Cl [pH 9.0], 1% SDS, 25 mM EDTA, and 0.4 M LiCl). The plant stature and fertility of F2 plants were scored according to the formation of siliques.

EXAMPLE 1

Screening and Isolation of an Arabidopsis Allene Oxide Synthase (AOS) Knock-Out Mutant Allene oxide synthase (AOS), a cytochrome P450 (CYP74A), is of particular importance in jasmonate biosynthesis because it catalyzes the a critical step in the JA-specific biosynthetic pathway, the dehydration of 13-(S)-hydroperoxylinolenic acid to 12,13-epoxy-linolenic acid (allene oxide) (FIG. 1). In Arabidopsis, only one copy of the AOS gene is present and alternative enzymes have not been reported to catalyze this step (Laudert et al. (1996) Plant Mol Biol 31:323–335).

Using a PCR-based reverse genetics screening method with CYP74A- and T-DNA border-specific primers on 72,750 T-DNA insertion lines, a knock-out mutant for CYP74A, witch is located on the Arabidopsis chromosome 5, was isolated from the TJ lines (TJ1180). The T-DNA in these transformants confers kanamycin-resistance (Kan$^R$). Four kanamycin-resistant seedlings from this pool contained the appropriate PCR product when AOS- and border-specific primers were used. PCR using two AOS-specific primers confirmed that three of the siblings were heterozygous and one (TJ1180-1) was homozygous for the insert. TJ1180-1 displayed complete sterility. FIG. 8 shows the AOS gene structure based on genomic and cDNA sequences and relative locations and directions of primers used to amplify gene-specific (CYP74A1F and CYP74A1R) and T-DNA flanking region-specific bands (TJRB and CYP74A1R). Analysis of the AOS flanking sequence in TJ1180-1 showed that the T-DNA insertion point was at −77 bp upstream of the heme binding domain, which is highly conserved and crucial for functionality of cytochrome P450 proteins.

The genomic sequence of each of the mutant alleles was determined by isolating genomic DNA from plants carrying each mutation. The genomic sequences of each mutant were amplified by PCR using the following primers: CYP74A1F, CYP74A1R, and TJRB. The TJRB primer was used to confirm the presence of T-DNA. Sequencing indicated that the mutants were both T-DNA inserts. FIG. 8 depicts the nucleotide sequence of native CYP74A gene locus, AOS gene, derived from *Arabidopsis thalianna* (GenBank Accession No. Y12636). In the figure, a transcription initiation signal is located from approximately bases 1,842 to 1,849, the wild-type mRNA corresponds to sequences from nucleotide position approximately 1,874 to 3,741, and the AOS protein coding sequences are from nucleotide position 1,951 to 3,507.

FIG. 2 shows a more detailed schematic map of the CYP74A (allele 1) locus which was identified from TJ line. The CYP74A gene and flanking genomic regions, designated by open box and lines are shown, respectively. The heme binding domain of CYP74A gene is indicated by closed box (Heme). The open triangle shows the T-DNA insertion in the exon region of CYP74A gene. Closed arrows show locations and directions of primers using to screen a CYP74A mutant (primers CYP74A1F, CYP74A1R, and TJRB) and to clone the CYP74A1 exon region (primers CYP74A1EF and CYP74A1ER).

EXAMPLE 2

Co-Segregation of Kanamycin Resistance and CYP74A

TJ1180-1 was back-crossed to wild-type and F1 and F2 progeny were analyzed for segregation of the sterility and $Kan$ phenotypes (Table 1). The 3:1 $Kan^R$:$Kan^S$ segregation ratio of F2 progeny indicates a single T-DNA insertion with a functional kanamycin resistance marker. In addition, $Kan^R$ wild-type fertile plants segregated in a 3:1 (wt:mut) manner for sterile plants indicating that sterility was caused by a recessive chromosomal mutation. The linkage of the sterile phenotype with the kanamycin resistance marker representing the T-DNA insertion was analyzed with 72 F2 segregating progenies. PCR analyses of 19 sterile F2 plants with AOS and border specific primers showed that all were homozygous for the aos T-DNA knock-out allele. Of 53 fertile plants, PCR analyses showed that 36 were heterozygous for the insertion while 17 plants lacked an insert. As such the segregation ratio of the F2 progeny was an acceptable 1:2:1 (wild-type:heterozygous:mutant; p>0.9) according to $\chi^2$ analysis (Table 1).

The results of the genetic, co-segregation analysis were as follows in Table 1.

TABLE 1

Co-segregation of kanamycin resistance and aos mutation.

| Genotypes | | Phenotypes | | $\chi^{2b}$ |
| --- | --- | --- | --- | --- |
| | | Fertile | Male sterile | |
| AOS/AOS | Parent | All | | |
| aos/aos | Parent | | All | |
| AOS/aos | F1 | 15 | 0 | |
| | F2$^a$ | 53(17 [W], 36 [H]) $Kan^R$ | 19 [M] $Kan^S$ | 0.111 |
| | F2 | 401 | 127 | 0.253 |

$^a$Total 72 F2 siblings were scored for the sterile phenotype. Genotypes of progenies were analyzed by PCR using gene specific and T-DNA specific primers (see FIG. 2). W: wild-type; H: heterozygous; M: homozygous mutant.
$^b$The $\chi^2$ values are for an expected ratio of 1:2:1 (p > 0.9) or 3:1 (p > 0.5).

These results show tight linkage of the sterility phenotype with the T-DNA insertion and suggest that the sterility phenotype was caused by a knock-out of AOS.

EXAMPLE 3

Whole Plant Phenotypes

A. Wild-Type and CYP74A Mutant Plants

*Arabidopsis thaliana* wild-type and CYP74A mutant plants were grown under standard culture conditions (see materials and methods).

*Arabidopsis thaliana* wild-type and CYP74A mutant plants were photographed 30 days after germination. A representative comparison of the plants is presented in FIG. 3. As shown in the figure, the 3rd and 4th siliques of wild-type (FIG. 3, Panel A, two open arrow heads) show normal development. Flowers of CYP74A1-1 mutant (FIG. 3, Panel B, two open arrow heads) fail to make siliques. The inset pictures show initial 3 siliques from the primary inflorescence of wild-type (Panel A) and CYP74A1-1 mutant (Panel B) at a week after flower opening. In the figure, the small white bar provides a scale where the bar=1 cm.

The plant phenotypes of the CYP74A is consistent with severe male sterile symptoms due to defects in anther and pollen production.

B. Expression Levels of CYP74A Gene

The expression levels of the CYP74A gene mRNA transcripts in wild-type and CYP74A mutant plants were evaluated. Total RNAs were isolated from rosette leaves of four week old plants. One microgram of total RNA from each sample was treated with DNase I. The treated samples were each then used as template for reverse transcription (RT) reactions. The RT products were diluted ten-fold and then one microliter of each diluted RT product was used as template for PCR amplification. The Actin-2 gene, which is strongly and constitutively expressed in *Arabidopsis*, was amplified as a control using the following primers: The amplification products were size-fractionated on 1.2% agarose gels containing 0.01% EtBR (Sigma, USA).

The results showed stable transcript corresponding to the CYP74A locus in RNA obtained from the wild-type plant. By comparison, RNA obtained from the CYP74A mutant plant showed essentially no stable transcript corresponding to the CYP74A locus.

These results suggest that the CYP74A mutation was essentially a knock-out mutation of the CYP74A gene.

EXAMPLE 4

Recovered Fertility of Cyp74A Mutant by the Exogenous Application of Methyl Jasmonic Acid The adult phenotype of an aos mutant plant is shown in FIG. 3. As compared to wild-type, aos mutants show no overt developmental defects, except for sterility. Following fertilization, siliques of wild-type plants elongated and the floral organs senesced within a week (FIG. 3, left). In the aos mutant, however, the floral organs senesced normally but the siliques remained small, producing no seeds (FIG. 3, right).

FIG. 4A shows an opened flower of wild-type and an aos mutant; petals and sepals were cut away to show the pistil and anthers. In wild-type plants, anthers develop fully and pollen dehisces on the stigmatic papilla (FIG. 4A, left). The fertilized pistil elongates to generate a silique containing the developing seeds. Following fertilization, other floral organs, such as sepals, petals, and anthers, senesced and fell away from the silique (FIG. 4B, left). Meanwhile in the aos mutant, stamen elongation and anther development were stalled at the flower opening stage (Smyth et al. (1990) *Plant Cell* 2:755–767) and the pollen failed to dehisce (FIG. 4A, right). Other processes, including floral development, and floral organ senescence were similar to wild-type. Anther development in aos mutants was completely blocked and failed to recover (FIG. 4A, right and 4B).

The AOS gene is important in jasmonate biosynthesis because it catalyzes the most upstream step in the JA-specific biosynthetic pathway (FIG. 1). We tested whether blocking jasmonate production caused the male sterile phenotype in the aos knock-out mutant as no alternative steps or enzymes have been shown to catalyze this step. To this end, we tested whether the male sterile phenotype could be rescued by the application of linolenic acid (LA), an initial substrate and starting material in jasmonate biosynthesis, oxo-phytodienoic acid (OPDA), an intermediate substrate and MeJA, a methyl ester of jasmonic acid.

FIG. 4A shows opened flowers of wild-type (left) and *Arabidopsis thaliana* CYP74A mutant (right). Anthers of the wild-type dehisced and pollens adhered to the stigmatic papilla (left open arrow head). The CYP74A anthers were not fully elongated and dehisced (right open arrow head). In Panel A, a scale is provided by the white bar, where the bar=1 mm.

FIG. 4B shows a male sterile aos mutant silique and an aos silique rescued to wild-type by application of OPDA and MeJA. Two days after OPDA and MeJA spraying, aos mutant siliques started to elongate and reached the wild-type silique size in a week, while LA-sprayed siliques did not respond. Seeds of OPDA and MeJA-rescued aos plants were collected and sown. All progeny showed the male sterile phenotype again confirming that they were selfed progeny of the aos mutant.

These results demonstrated that exogenous application of jasmonic acid to plants bearing CYP74A3 mutations resulted in restoration of essentially wild-type siliques and recovered fertility in mutant plants. Thus, application of MeJA can rescue the aos male sterile phenotype.

EXAMPLE 5

Constitutive AOS Expression Complements the Male Sterile Phenotype of aos Mutants Co-segregation of the T-DNA insert with male sterility and chemical complementation of the male sterile phenotype in aos mutants with MeJA provided strong evidence that the male sterility in aos was caused by a disruption of AOS. However, to remove any possibility that the male sterile phenotype was caused by an unknown mutation, it was important to show that expression of AOS could complement the aos mutant phenotype. For functional complementation of the aos mutation, transgenic lines carrying AOS under the control of the cauliflower mosaic virus (CaMV) 35S promoter in wild-type plants were generated (see methods).

To introduce the constitutive AOS construct into aos mutants, AOS-OE lines were crossed to aos mutants as male parent. Twelve F1 plants, resulting from crosses with 3 independent overexpression lines, were selfed to get F2 segregating families. To isolate seedlings carrying both the aos knock-out mutation and the constitutive AOS construct, F2 seeds were germinated in the presence of kanamycin and hygromycin, their respective selection markers. Six F2 progeny for each F1 parent that were resistant to both antibiotics, were selected and transferred to soil. The genotypes of the transferred plants were tested by PCR using specific primer sets for aos, AOS, and the constitutive AOS expression (AOS-OE) construct and male sterility was examined at the flowering stage. All 72 plants showed normal fertility and silique elongation (FIG. 5A). To identify genotypes of selected F2 plants, sets of primers were used to amplify the wild-type AOS, T-DNA inserted aos, and constitutively expressed AOS specific bands, respectively. FIG. 5B shows their orientation and relative locations on a schematic drawing of the aos and constitutive AOS gene structure. Genotyping results indicated that 26 out of 72 plants were homozygous for the aos mutation and contained an AOS-OE construct (FIG. 5C). From these results, it is clear that the male sterility phenotype in the aos mutant is completely rescued by the AOS-OE construct.

EXAMPLE 6

Figure 6:
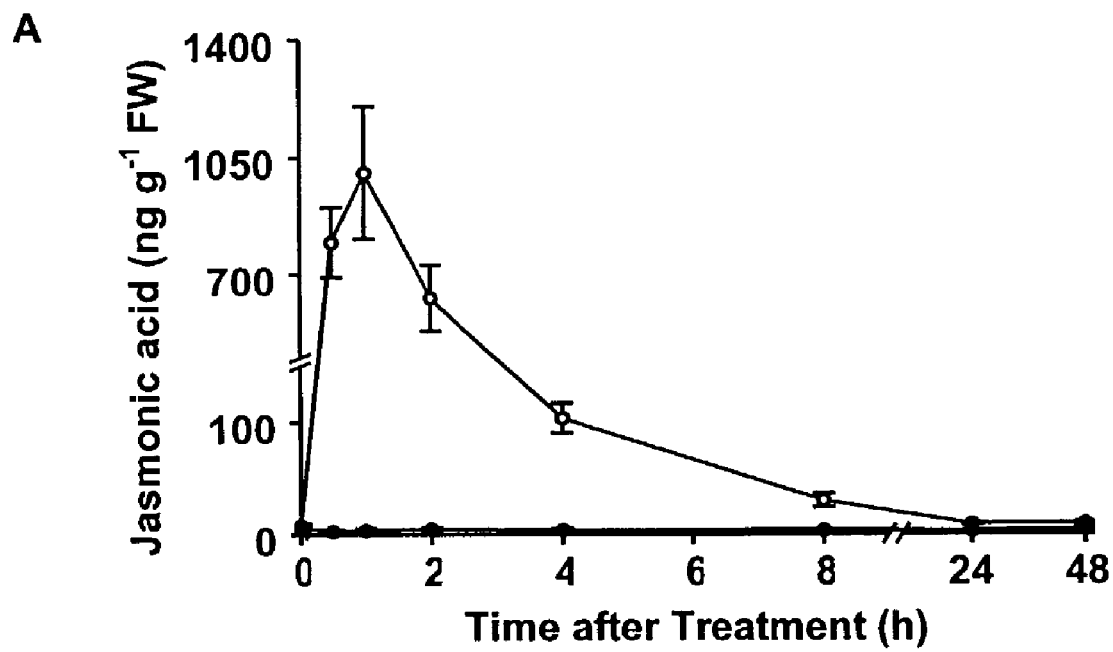
FIG. 6 shows induction of jasmonates and jasmonate inducible genes by wound treatment. Panel (A) depicts the kinetics of wound induced JA levels (Mean±SE of 4 replicates) of wild-type (Col-6, open circles) and aos (closed circles) *Arabidopsis* plants. Panel (B) is a reproduction of a gel and shows amplification by RT-PCR of AtLOX2, AOS, AtVSP2 genes after wound treatment, respectively. Total RNA was isolated from wounded leaves of wild-type plants and aos mutants at 2, 4, and 8 hour after wounding. As a control, *Arabidopsis* ACTIN-2 gene was amplified.
Figure 6:
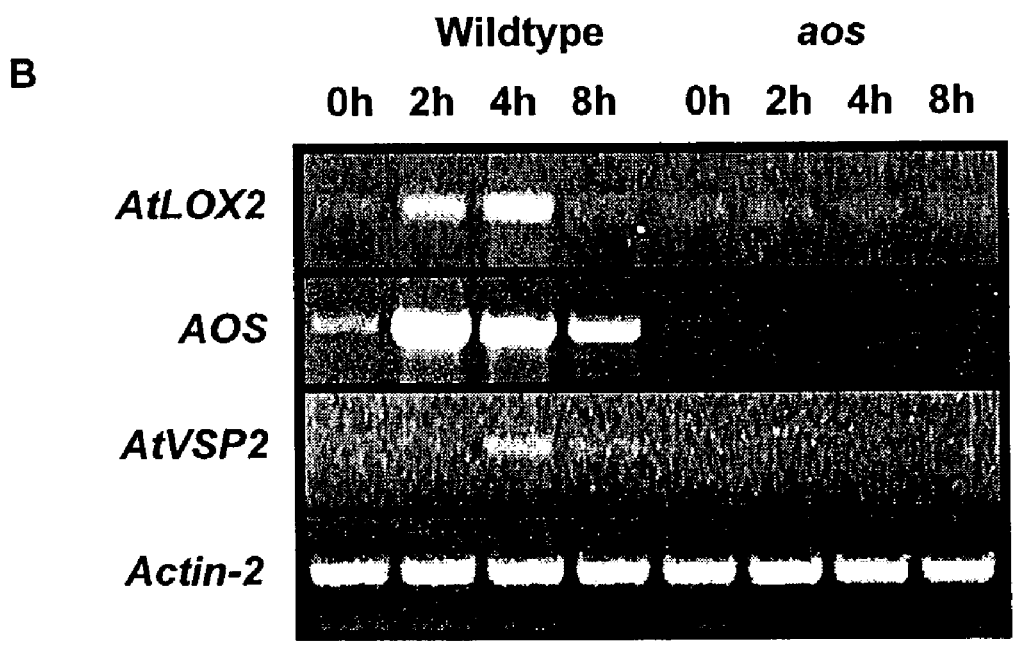

The AOS Knock-Out Mutation Blocks Wound Signal Transduction as well as Jasmonic Acid Biosynthesis We then investigated whether jasmonic acid biosynthesis is blocked in the aos mutant by measuring internal jasmonate levels in wild-type Col-6 and aos mutant plants after wounding. In the absence of wounding or pathogen attack, the level of JAs are barely detectable in *Arabidopsis* (Creelman et al. (1992) *PNAS USA* 89:4938–4941; Kramell et al. (2000) *Plant Physiol* 123:177–188; Weichert et al. (2000) *Biocehm Soc Trans.* 28:861–862). After wound treatment, jasmonate levels were dramatically increased and reached a peak one hour after wounding (FIG. 6A). Internal jasmonate concentration returned to normal levels one day after wounding. In contrast, aos mutants showed no induction of jasmonic acid after wounding, and internal jasmonate levels were not significantly different from unwounded wild-type plants (P's>0.93). The induction kinetics of JA accumulation indicate that jasmonate biosynthesis is completely blocked by the aos mutation in *Arabidopsis*.

Figure 7:
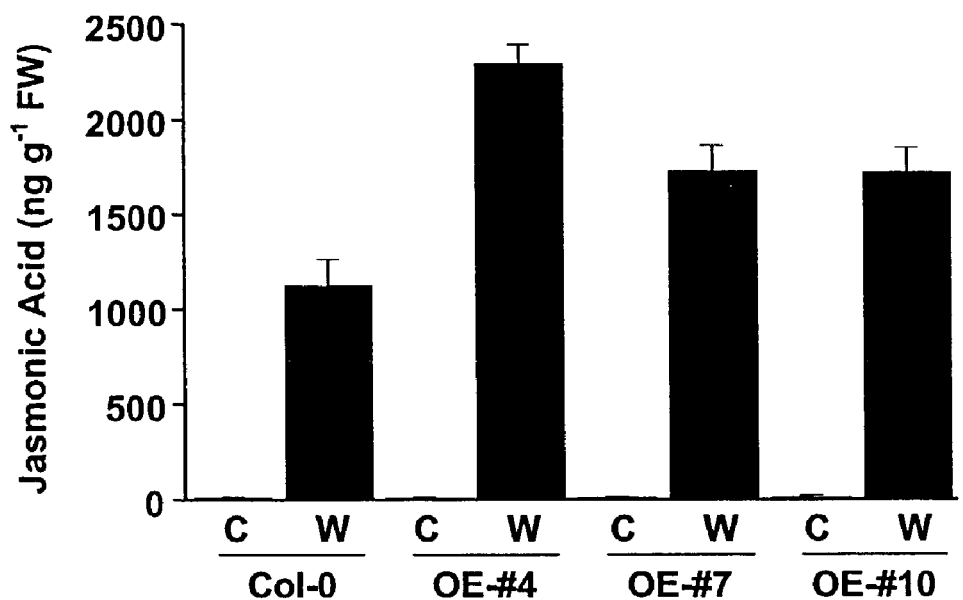
FIG. 7 depicts jasmonic acid (JA) content and expression levels of jasmonate inducible genes in AOS over-expression lines. Panel (A) shows mean JA levels of wild-type (Col-0) and CYP74A overexpressing (OE-#4, OE-#7, OE-#10) *Arabidopsis* plants (5 replicates per treatment). Samples were taken 1 h after wound treatment (W) or from undamaged control plants (C). Panel B shows amplification by RT-PCR of AtLOX2, AOS, AtVSP2 genes after wound treatment, respectively. Total RNA was isolated from wounded leaves of wild-type plants and transgenic lines carrying AOS-OE # 7 construct at 0.5, 1, 2, 4, and 8 hour after wounding. The *Arabidopsis* ACTIN-2 gene was amplified as a control.
Figure 7:
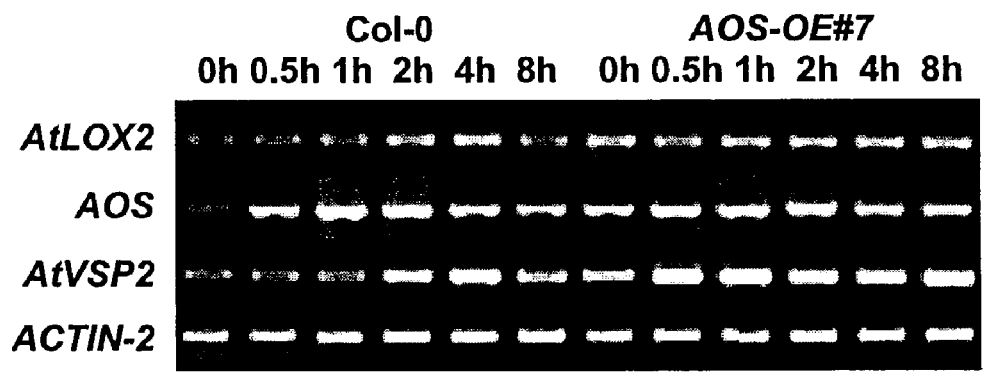

Jasmonic acid and methyl jasmonate have been reported to perform roles in wound responses in plants (Gundlach et al. (1992) *Proc Natl Acad Sci USA* 89(6):2389–93), as well as in developmental processes (Sembdner and Parthier (1993) *Annu. Rev. Plan Physiol.* 54:328–332; Creelman and Mullet (1997) *Plant Physiol. Plant Mol. Biol.* 48:355–381). To investigate wound responses in aos mutants, expression levels of AOS, *A. thaliana* vegetative storage protein2 (AtVSP2), and lipoxygenase2 (AtLOX2), which are known as wound and jasmonate responsive genes (Laudert and Weiler (1998) *Plant J.* 15:675–684; Utsugi et al. (1998) *Plant Mol Biol.* 38:565–576; Bell and Mullet (1993) *Plant Physiol.* 103:1133–1137), were examined by RT-PCR after wound treatment (FIGS. 6B and 7B). The expression level of AOS was maximally induced 2 hours after treatment and then decreased gradually to near normal levels in wild-type, consistent with results of jasmonate levels. In aos mutants, AOS transcripts were not detected even in wound induced conditions, indicating that the T-DNA insertion prevents the accumulation of any transcript from this gene (FIG. 6B). Two other wound inducible genes, AtVSP2 and AtLOX2, reached maximum transcript levels 4 hours after treatment in wildtype and rapidly decreased to normal expression levels. Interestingly, their expression levels in aos mutant were not affected by wound treatment, indicating that the wound signal to AtLOX2 and AtVSP2 was severed by the aos mutation (FIG. 6B).

Thus, the biosynthesis of all biologically active jasmonates was blocked by the aos mutation and wound signal transduction to AtLOX2 and AtVSP2 was interrupted by blocking JA production.

EXAMPLE 7

Constitutive Expression of AOS Causes an Increase in Wounding-Induced JA Levels

Three transgenic lines expressing AOS under control of the CAMV 35S promoter were analyzed for their JA levels and for the relative AOS, AtLOX2 and AtVSP2 transcript levels as was done for the aos mutant plants. JA levels in healthy AOS-OE plants were similar to that in wild-type plants, but one hour after wounding JA reached levels far superior to those observed in wounded wild-type plants (FIG. 7A). In line AOS-OE #4 wound-induced JA levels were doubled to over 2.2 μg/g FW, thus confirming the results of Laudert et al. (2000) *Planta* 211:163–165.

RT-PCR experiments showed that AOS, AtLOX2 and AtVSP2 were induced faster in the AOS-OE lines than in wild-type plants. (FIG. 6B). Transcript levels in unwounded AOS-OE plants also appeared higher than in their wild-type counterparts, perhaps indicating an exquisite sensitivity of these plants to JA.

In sum, our results support the notion that AOS is critical in the biosynthesis of all biologically active JAs and is a major regulator of the wound signal transduction pathway in *Arabidopsis*.

Although preferred embodiments of the subject invention have been described in some detail, it is understood that obvious variations can be made without departing from the spirit and the scope of the invention as set forth herein.

What is claimed is:

1. A transgenic plant transformed with a polynucleotide encoding a CYP74A polypeptide, wherein said polynucleotide is operably linked to a tissue-specific promoter, and wherein CYP74A is underexpressed as compared to a wild-type plant.

2. A method of producing a transgenic plant having altered CYP74A expression relative to the wild-type plant, said method comprising:

(a) introducing into a plant cell an expression construct that comprises a polynucleotide encoding a CYP74A polypeptide operably linked to a tissue-specific promoter to produce a transformed plant cell; and (b) producing a transgenic plant from the transformed plant cell, wherein CYP74A is underexpressed as compared to a wild-type plant.

* * * * *

SEQUENCE LISTING

```
<160> NUMBER OF SEQ ID NOS: 27

<210> SEQ ID NO 1
<211> LENGTH: 4188
<212> TYPE: DNA
<213> ORGANISM: Arabidopsis thaliana
<220> FEATURE:
<221> NAME/KEY: CDS
<222> LOCATION: (1951)...(3504)

<400> SEQUENCE: 1
aagctttacc aaaaaagtac aatggtgata tatatttggt tagtttgacc agtgagaatg      60
cattttatca catttatgta aaccactcaa caaagaacct ctagcaagcg tcggacaaga     120
agtttaagat tactaaggcc agaattaatt actaccttgt tcacatgttg tatgatcatc     180
gtagcataat gtcttagaac aaacagatca gctacatgtt aagctctacg accaaaatgt     240
tgaagggctc gaggctaatg tagtttggtg tctcttatga aaaagctact ccacagaggc     300
ttcaaatatt atcttttaag cacaagacac atgcgattaa agtagcattg aggacttcgt     360
gattgtgatt acttccatgt aacgccctcg atgcaaatta aaaatgttgt tttcatcaat     420
agccactcct aactcggaag tgtttagtta tgacaatcaa aaacttaaga gaattttctg     480
tgtattccaa tatgttatga ggtttattca aagagaagga gacctaagta ttttctttcc     540
aacaaggcaa aaaacaggta aacgcttgag acaaatatta tcatgtttgt ccaaaaatag     600
tgagtatcat gtgaataatt tagaagctag atatgttcgt caataaacaa taaaatgcgc     660
taggatacaa aacgaacgct tgggacgtgt tttaggtaca aaacttcaaa aaaatcttta     720
tcgagacaga tttccagata aaatacacat accatttttaa caacgtgtgt gtttatacaa     780
aaataacaaa atattaattt tacgatttga agatatatat tgtcagaagg ggaaaagaaa     840
aaaacaaaac aaaaagatac aaaacagagt aacaaactct ataaaatatg ataatataat     900
acataattgg gaaaatgact aaacattatc tctgccttttt ggaactcatc aataattata     960 tatttttta ttctcataa aagtcaaaac tatcaattct taaattcatt ctaattcact    1020
caactttttt ttataaaaaa atatctatat taagttctcg atattattta cttccattaa    1080
tttatcaaat gattttggta tagaatcaac ttataatcat ggatcaagtc gtggaataac    1140
atatgctcaa gggatggagc taaaagtgca gtctaccaaa cctcaagtgt ttgtaacttt    1200
```

-continued

```
gtataagcta ggcctccgat tattaactga atcggttttt ctggatcaaa ccaaactgag    1260
atttggggtt tggttaaccg tccggtttat aagagtcagc cagtcagtta gatttttgaaa   1320 taaggtcgga taacagtttg gtttggttta tcgaaccaaa cggttaacca tttgtttaaa    1380 atttttccaat ttaataattt tacggatatt ttacgtaatg atatcaaaaa ttcttcaaaa   1440
cactacgtga accaaaaaaa aactattcaa atatttttaa agtctcaaat gcttgtataa    1500
actattgata gtacattttc aggatatatt ataagaagag gaatattaaa caaagaaaca    1560
aaaatacaaa acagagcaac aagctcgata aaatatgaga ataaatagta ccaacttta    1620 cacaacaaaa acattaccaa ttttttaata tgtcagaaaa aataaaaaaa gtaccaactt    1680
tataaaatga aggaaaaaag agtcaaagca cgtggctaaa tgaatcggcc ggtggccaga    1740
gtctccaata gatctcttta taactgcgt ggtctgaaaa aggaatcttc cttccacggc     1800
cactaaattc actattttca ttcacattta ttattttcct ttataaatac aaattcattt    1860
ctacacaata atcattcaat acacataatt tacttctttc tttataacta ccatattctc    1920
aatcacaaca ctcgccactg tttcgaatag atg gct tct att tca acc cct ttt    1974
                                    Met Ala Ser Ile Ser Thr Pro Phe
                                     1               5 ccg att tct ctc cac cca aaa acc gta cga tca aag ccg ttg aaa ttc    2022
Pro Ile Ser Leu His Pro Lys Thr Val Arg Ser Lys Pro Leu Lys Phe
     10                  15                  20 cga gtt ttg acc cgt ccg atc aaa gct tcc ggg tca gaa act cct gat    2070
Arg Val Leu Thr Arg Pro Ile Lys Ala Ser Gly Ser Glu Thr Pro Asp
 25                  30                  35                  40 cta acc gta gcg aca cga acc gga tcc aaa gat ctc ccg atc cga aac    2118
Leu Thr Val Ala Thr Arg Thr Gly Ser Lys Asp Leu Pro Ile Arg Asn
                 45                  50                  55 ata ccg gga aac tac ggt tta cca atc gta gga cca atc aaa gac cgt    2166
Ile Pro Gly Asn Tyr Gly Leu Pro Ile Val Gly Pro Ile Lys Asp Arg
             60                  65                  70 tgg gat tac ttt tac gac caa gga gct gaa gag ttc ttc aaa tca cga    2214
Trp Asp Tyr Phe Tyr Asp Gln Gly Ala Glu Glu Phe Phe Lys Ser Arg
         75                  80                  85 atc cgt aaa tac aac tcc acg gtg tac aga gtc aac atg cca ccg gga    2262
Ile Arg Lys Tyr Asn Ser Thr Val Tyr Arg Val Asn Met Pro Pro Gly
     90                  95                 100 gct ttt atc gcc gag aat cca caa gtc gtg gct tta ctc gac ggt aaa    2310
Ala Phe Ile Ala Glu Asn Pro Gln Val Val Ala Leu Leu Asp Gly Lys
105                 110                 115                 120 agc ttc ccg gtt tta ttc gat gtc gat aaa gtc gaa aag aaa gat ctt    2358
Ser Phe Pro Val Leu Phe Asp Val Asp Lys Val Glu Lys Lys Asp Leu
                125                 130                 135 ttc acc ggt act tac atg ccg tca acg gaa cta acc gga ggc tac cgt    2406
Phe Thr Gly Thr Tyr Met Pro Ser Thr Glu Leu Thr Gly Gly Tyr Arg
            140                 145                 150 atc ctc tcg tac ctc gat cca tcg gag cct aaa cac gaa aag ctc aaa    2454
Ile Leu Ser Tyr Leu Asp Pro Ser Glu Pro Lys His Glu Lys Leu Lys
        155                 160                 165 aat ctc ctt ttc ttc ctc ctc aag tca tct cga aac cgg atc ttc cct    2502
Asn Leu Leu Phe Phe Leu Leu Lys Ser Ser Arg Asn Arg Ile Phe Pro
    170                 175                 180 gag ttt caa gct act tac tcc gag ctt ttc gat tct ttg gag aaa gag    2550
Glu Phe Gln Ala Thr Tyr Ser Glu Leu Phe Asp Ser Leu Glu Lys Glu
185                 190                 195                 200 ctt tcc ctt aaa ggg aaa gcg gat ttc ggc ggt tcc agc gac gga acc    2598
Leu Ser Leu Lys Gly Lys Ala Asp Phe Gly Gly Ser Ser Asp Gly Thr
```

-continued

|  |  |  |  |  |  |  |  |  |  |  |  |  |  |
|---|---|---|---|---|---|---|---|---|---|---|---|---|---|
|  |  | 205 |  |  |  | 210 |  |  |  | 215 |  |  |  |
| gcc | ttt | aat | ttc | ttg | gct | cga | gct | ttc | tac | ggg | acg | aat | ccc gca gat | 2646 |
| Ala | Phe | Asn | Phe | Leu | Ala | Arg | Ala | Phe | Tyr | Gly | Thr | Asn | Pro Ala Asp |  |
|  |  | 220 |  |  |  | 225 |  |  |  | 230 |  |  |  |
| aca | aag | ctc | aaa | gcc | gac | gct | ccg | ggt | ttg | atc | act | aaa | tgg gtt tta | 2694 |
| Thr | Lys | Leu | Lys | Ala | Asp | Ala | Pro | Gly | Leu | Ile | Thr | Lys | Trp Val Leu |  |
|  | 235 |  |  |  |  | 240 |  |  |  |  | 245 |  |  |
| ttc | aat | ctc | cat | cca | tta | ctc | tct | att | ggt | tta | ccg | aga | gtt ata gaa | 2742 |
| Phe | Asn | Leu | His | Pro | Leu | Leu | Ser | Ile | Gly | Leu | Pro | Arg | Val Ile Glu |  |
|  | 250 |  |  |  |  | 255 |  |  |  |  | 260 |  |  |
| gaa | cct | ctc | atc | cat | aca | ttt | agt | cta | cca | ccg | gcg | tta | gtc aaa tct | 2790 |
| Glu | Pro | Leu | Ile | His | Thr | Phe | Ser | Leu | Pro | Pro | Ala | Leu | Val Lys Ser |  |
| 265 |  |  |  |  | 270 |  |  |  |  | 275 |  |  | 280 |
| gat | tac | cag | aga | ctc | tac | gag | ttt | ttc | tta | gaa | tcc | gcc | ggt gag att | 2838 |
| Asp | Tyr | Gln | Arg | Leu | Tyr | Glu | Phe | Phe | Leu | Glu | Ser | Ala | Gly Glu Ile |  |
|  |  |  | 285 |  |  |  |  | 290 |  |  |  |  | 295 |
| ctc | gtt | gaa | gcc | gat | aaa | ttg | ggt | atc | tca | cga | gaa | gaa | gct act cac | 2886 |
| Leu | Val | Glu | Ala | Asp | Lys | Leu | Gly | Ile | Ser | Arg | Glu | Glu | Ala Thr His |  |
|  |  |  | 300 |  |  |  |  | 305 |  |  |  |  | 310 |
| aat | ctt | ctc | ttc | gcc | acg | tgc | ttc | aac | acg | tgg | ggt | ggg | atg aag att | 2934 |
| Asn | Leu | Leu | Phe | Ala | Thr | Cys | Phe | Asn | Thr | Trp | Gly | Gly | Met Lys Ile |  |
|  |  | 315 |  |  |  |  | 320 |  |  |  |  | 325 |  |
| ttg | ttt | ccg | aat | atg | gtt | aaa | cgt | atc | ggg | cgg | gcg | ggt | cat caa gtt | 2982 |
| Leu | Phe | Pro | Asn | Met | Val | Lys | Arg | Ile | Gly | Arg | Ala | Gly | His Gln Val |  |
|  | 330 |  |  |  |  | 335 |  |  |  |  | 340 |  |  |
| cat | aac | cga | tta | gcg | gag | gag | att | aga | tct | gtg | att | aaa | tcc aac ggc | 3030 |
| His | Asn | Arg | Leu | Ala | Glu | Glu | Ile | Arg | Ser | Val | Ile | Lys | Ser Asn Gly |  |
| 345 |  |  |  |  | 350 |  |  |  |  | 355 |  |  |  | 360 |
| gga | gaa | ctc | acg | atg | gga | gcg | att | gag | aaa | atg | gag | tta | acc aaa tca | 3078 |
| Gly | Glu | Leu | Thr | Met | Gly | Ala | Ile | Glu | Lys | Met | Glu | Leu | Thr Lys Ser |  |
|  |  |  | 365 |  |  |  |  | 370 |  |  |  |  | 375 |
| gtg | gtt | tac | gaa | tgt | ctc | cgg | ttt | gaa | cca | ccg | gtt | acg | gct caa tac | 3126 |
| Val | Val | Tyr | Glu | Cys | Leu | Arg | Phe | Glu | Pro | Pro | Val | Thr | Ala Gln Tyr |  |
|  |  | 380 |  |  |  |  | 385 |  |  |  |  | 390 |  |
| ggt | aga | gcg | aag | aag | gat | ctg | gtt | atc | gaa | agc | cac | gac | gcg gcg ttt | 3174 |
| Gly | Arg | Ala | Lys | Lys | Asp | Leu | Val | Ile | Glu | Ser | His | Asp | Ala Ala Phe |  |
|  | 395 |  |  |  |  | 400 |  |  |  |  | 405 |  |  |
| aaa | gtc | aaa | gcc | ggt | gaa | atg | ctt | tac | ggt | tat | caa | ccg | ttg gcg acg | 3222 |
| Lys | Val | Lys | Ala | Gly | Glu | Met | Leu | Tyr | Gly | Tyr | Gln | Pro | Leu Ala Thr |  |
| 410 |  |  |  |  | 415 |  |  |  |  | 420 |  |  |  |
| aga | gat | ccg | aag | att | ttt | gat | cgg | gcg | gat | gag | ttt | gtg | ccg gag aga | 3270 |
| Arg | Asp | Pro | Lys | Ile | Phe | Asp | Arg | Ala | Asp | Glu | Phe | Val | Pro Glu Arg |  |
| 425 |  |  |  |  | 430 |  |  |  |  | 435 |  |  |  | 440 |
| ttc | gtc | gga | gaa | gaa | gga | gag | aag | ctt | ttg | agg | cat | gtg | ttg tgg tcg | 3318 |
| Phe | Val | Gly | Glu | Glu | Gly | Glu | Lys | Leu | Leu | Arg | His | Val | Leu Trp Ser |  |
|  |  |  | 445 |  |  |  |  | 450 |  |  |  |  | 455 |
| aat | gga | ccg | gag | acg | gag | act | ccg | acg | gtg | ggg | aat | aaa | caa tgc gcc | 3366 |
| Asn | Gly | Pro | Glu | Thr | Glu | Thr | Pro | Thr | Val | Gly | Asn | Lys | Gln Cys Ala |  |
|  |  | 460 |  |  |  |  | 465 |  |  |  |  | 470 |  |
| ggt | aag | gat | ttt | gtt | gtt | ttg | gtg | gcg | agg | ttg | ttt | gtg | att gag att | 3414 |
| Gly | Lys | Asp | Phe | Val | Val | Leu | Val | Ala | Arg | Leu | Phe | Val | Ile Glu Ile |  |
|  | 475 |  |  |  |  | 480 |  |  |  |  | 485 |  |  |
| ttc | cgg | cga | tat | gat | tcg | ttt | gat | att | gag | gtt | ggt | acg | tcg ccg tta | 3462 |
| Phe | Arg | Arg | Tyr | Asp | Ser | Phe | Asp | Ile | Glu | Val | Gly | Thr | Ser Pro Leu |  |
|  | 490 |  |  |  |  | 495 |  |  |  |  | 500 |  |  |
| gga | agc | tcc | gtt | aat | ttc | tcg | tcg | tta | agg | aaa | gct | agc | ttt |  | 3504 |
| Gly | Ser | Ser | Val | Asn | Phe | Ser | Ser | Leu | Arg | Lys | Ala | Ser | Phe |  |  |
| 505 |  |  |  |  | 510 |  |  |  |  | 515 |  |  |  | taggagccaa gggtaaattt gtaattgtat atgttcgcac ctgtgtagtc catctgtttt    3564

-continued

```
cttgttccag tttcgtgaat tttgagaaaa tgttgtataa tctgttgctg ctctacatgt    3624 tcgtttttt  gtcataatat taaagttcaa gctggtaata agtatttaca aatctgtgag    3684
ataatttcaa atacacaaga gcatattctt tataaaaaaa gcacgagttt tttacactca    3744
aatatttttt gagcctgtga ataatagggt ttttttaacc attgttttta ttttgttagt    3804
gacgaaacaa ataacaaaa  atatcaccgt taaagtttga ttatgagatg ttataaaaga    3864
gtgtattttc ctgcatacca aaataattct tgtactttta taaaaccgaa tgtttccgtt    3924
tatatagtgc aataattttt tagaatattt gttttaataa tacccataca caattttctg    3984
ttttaagcct tttatgtatt atcgtcagct ttcttaatga agataataaa agaaatcttc    4044
tgaaagatgg ttagatgggg ctggtaattt ggagttttgc ttatctctct ctggttaagt    4104
ctctttcctt gcgttgtgtg gagcctatgt ctatctctcg gtgacgactg atgagtgtct    4164
agaagtgata gagtctaggg atcc                                           4188
```

<210> SEQ ID NO 2
<211> LENGTH: 518
<212> TYPE: PRT
<213> ORGANISM: Arabidopsis thaliana

<400> SEQUENCE: 2

```
Met Ala Ser Ile Ser Thr Pro Phe Pro Ile Ser Leu His Pro Lys Thr
  1               5                  10                  15

Val Arg Ser Lys Pro Leu Lys Phe Arg Val Leu Thr Arg Pro Ile Lys
                 20                  25                  30

Ala Ser Gly Ser Glu Thr Pro Asp Leu Thr Val Ala Thr Arg Thr Gly
             35                  40                  45

Ser Lys Asp Leu Pro Ile Arg Asn Ile Pro Gly Asn Tyr Gly Leu Pro
         50                  55                  60

Ile Val Gly Pro Ile Lys Asp Arg Trp Asp Tyr Phe Tyr Asp Gln Gly
 65                  70                  75                  80

Ala Glu Glu Phe Phe Lys Ser Arg Ile Arg Lys Tyr Asn Ser Thr Val
                 85                  90                  95

Tyr Arg Val Asn Met Pro Pro Gly Ala Phe Ile Ala Glu Asn Pro Gln
                100                 105                 110

Val Val Ala Leu Leu Asp Gly Lys Ser Phe Pro Val Leu Phe Asp Val
            115                 120                 125

Asp Lys Val Glu Lys Lys Asp Leu Phe Thr Gly Thr Tyr Met Pro Ser
        130                 135                 140

Thr Glu Leu Thr Gly Gly Tyr Arg Ile Leu Ser Tyr Leu Asp Pro Ser
145                 150                 155                 160

Glu Pro Lys His Glu Lys Leu Lys Asn Leu Leu Phe Phe Leu Leu Lys
                165                 170                 175

Ser Ser Arg Asn Arg Ile Phe Pro Glu Phe Gln Ala Thr Tyr Ser Glu
            180                 185                 190

Leu Phe Asp Ser Leu Glu Lys Glu Leu Ser Leu Lys Gly Lys Ala Asp
        195                 200                 205

Phe Gly Gly Ser Ser Asp Gly Thr Ala Phe Asn Phe Leu Ala Arg Ala
    210                 215                 220

Phe Tyr Gly Thr Asn Pro Ala Asp Thr Lys Leu Lys Ala Asp Ala Pro
225                 230                 235                 240

Gly Leu Ile Thr Lys Trp Val Leu Phe Asn Leu His Pro Leu Leu Ser
                245                 250                 255
```

-continued

```
Ile Gly Leu Pro Arg Val Ile Glu Glu Pro Leu Ile His Thr Phe Ser
            260                 265                 270
Leu Pro Pro Ala Leu Val Lys Ser Asp Tyr Gln Arg Leu Tyr Glu Phe
        275                 280                 285
Phe Leu Glu Ser Ala Gly Glu Ile Leu Val Glu Ala Asp Lys Leu Gly
    290                 295                 300
Ile Ser Arg Glu Glu Ala Thr His Asn Leu Leu Phe Ala Thr Cys Phe
305                 310                 315                 320
Asn Thr Trp Gly Gly Met Lys Ile Leu Phe Pro Asn Met Val Lys Arg
                325                 330                 335
Ile Gly Arg Ala Gly His Gln Val His Asn Arg Leu Ala Glu Glu Ile
            340                 345                 350
Arg Ser Val Ile Lys Ser Asn Gly Gly Glu Leu Thr Met Gly Ala Ile
        355                 360                 365
Glu Lys Met Glu Leu Thr Lys Ser Val Val Tyr Glu Cys Leu Arg Phe
    370                 375                 380
Glu Pro Pro Val Thr Ala Gln Tyr Gly Arg Ala Lys Lys Asp Leu Val
385                 390                 395                 400
Ile Glu Ser His Asp Ala Ala Phe Lys Val Lys Ala Gly Glu Met Leu
                405                 410                 415
Tyr Gly Tyr Gln Pro Leu Ala Thr Arg Asp Pro Lys Ile Phe Asp Arg
            420                 425                 430
Ala Asp Glu Phe Val Pro Glu Arg Phe Val Gly Glu Gly Glu Lys
        435                 440                 445
Leu Leu Arg His Val Leu Trp Ser Asn Gly Pro Glu Thr Glu Thr Pro
    450                 455                 460
Thr Val Gly Asn Lys Gln Cys Ala Gly Lys Asp Phe Val Val Leu Val
465                 470                 475                 480
Ala Arg Leu Phe Val Ile Glu Ile Phe Arg Arg Tyr Asp Ser Phe Asp
                485                 490                 495
Ile Glu Val Gly Thr Ser Pro Leu Gly Ser Ser Val Asn Phe Ser Ser
            500                 505                 510
Leu Arg Lys Ala Ser Phe
        515
```

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
aacatatgct caagggatgg agctaaaag                                      29

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
cgaacatgta gagcagcaac tgattataca                                     30

<210> SEQ ID NO 5
<211> LENGTH: 28
<212> TYPE: DNA

```
<213> ORGANISM: Artificial Sequence
<220> FEATURE:
<223> OTHER INFORMATION: primer

<400> SEQUENCE: 5
ctttcgccta taaatacgac ggatcgta                                          28

<210> SEQ ID NO 6
<211> LENGTH: 28
<212> TYPE: DNA
<213> ORGANISM: Artificial Sequence
<220> FEATURE:
<223> OTHER INFORMATION: primer

<400> SEQUENCE: 6
cgggcctaac ttttggtgtg atgatgct                                          28

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7
gatgcactcg aaatcagcca attttagac                                         29

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8
tccttcaatc gttgcggttc tgtcagttc                                         29

<210> SEQ ID NO 9
<211> LENGTH: 29
<212> TYPE: DNA
<213> ORGANISM: Artificial Sequence
<220> FEATURE:
<223> OTHER INFORMATION: primer

<400> SEQUENCE: 9
cattttataa taacgctgcg gacatctac                                         29

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
tttctccata ttgaccatca tactcattg                                         29

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
acatcacgaa ttcaacaata aaccatacca t                                      31
```

<210> SEQ ID NO 12
<211> LENGTH: 31
<212> TYPE: DNA
<213> ORGANISM: Artificial Sequence
<220> FEATURE:
<223> OTHER INFORMATION: primer

<400> SEQUENCE: 12
ggagaattcg atgaagatag attcttaaga a                           31

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
ttggctgagg aagataagac cgcagaacat                             30

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
tcattttatc aagaagacag agatacagaa                             30

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
ccatattcta gatcacaaca ctcgccactg                             30

<210> SEQ ID NO 16
<211> LENGTH: 31
<212> TYPE: DNA
<213> ORGANISM: Artificial Sequence
<220> FEATURE:
<223> OTHER INFORMATION: primer

<400> SEQUENCE: 16
cagattctag aacattttct caaaattcac g                           31

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
ggagcctaaa cacgaaaagc tc                                     22

<210> SEQ ID NO 18
<211> LENGTH: 22
<212> TYPE: DNA
<213> ORGANISM: Artificial Sequence
<220> FEATURE:

<223> OTHER INFORMATION: primer

<400> SEQUENCE: 18
ttaactccat tttctcaatc gc					22

<210> SEQ ID NO 19
<211> LENGTH: 28
<212> TYPE: DNA
<213> ORGANISM: Artificial Sequence
<220> FEATURE:
<223> OTHER INFORMATION: primer

<400> SEQUENCE: 19
caatacgagg tcgccaacat cttcttct					28

<210> SEQ ID NO 20
<211> LENGTH: 28
<212> TYPE: DNA
<213> ORGANISM: Artificial Sequence
<220> FEATURE:
<223> OTHER INFORMATION: primer

<400> SEQUENCE: 20
caactctatc agagcttggt tgacggca					28

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
ctgtgtagaa gtactcgccg atagtggaaa					30

<210> SEQ ID NO 22
<211> LENGTH: 28
<212> TYPE: DNA
<213> ORGANISM: Artificial Sequence
<220> FEATURE:
<223> OTHER INFORMATION: primer

<400> SEQUENCE: 22
cactggccgt cgttttacaa cgtcgtga					28

<210> SEQ ID NO 23
<211> LENGTH: 25
<212> TYPE: DNA
<213> ORGANISM: Artificial Sequence
<220> FEATURE:
<223> OTHER INFORMATION: primer

<400> SEQUENCE: 23
gcaccgatcg cccttcccaa cagtt					25

<210> SEQ ID NO 24
<211> LENGTH: 28
<212> TYPE: DNA
<213> ORGANISM: Artificial Sequence
<220> FEATURE:
<223> OTHER INFORMATION: primer

<400> SEQUENCE: 24
cagattgtcg tttcccgcct tcagttta					28

```
<210> SEQ ID NO 25
<211> LENGTH: 32
<212> TYPE: DNA
<213> ORGANISM: Artificial Sequence
<220> FEATURE:
<223> OTHER INFORMATION: primer

<400> SEQUENCE: 25
gtacgatcaa agccgttgaa attccgagtt tt                              32

<210> SEQ ID NO 26
<211> LENGTH: 31
<212> TYPE: DNA
<213> ORGANISM: Artificial Sequence
<220> FEATURE:
<223> OTHER INFORMATION: primer

<400> SEQUENCE: 26
tggaacaaga aaacagatgg actacacagg t                               31

<210> SEQ ID NO 27
<211> LENGTH: 28
<212> TYPE: DNA
<213> ORGANISM: Artificial Sequence
<220> FEATURE:
<223> OTHER INFORMATION: primer

<400> SEQUENCE: 27
ctcattaggc accccaggct ttacactt                                   28
```